United States Patent
Benoff et al.

(10) Patent No.: US 6,833,244 B1
(45) Date of Patent: Dec. 21, 2004

(54) OLIGONUCLEOTIDES FOR DETECTING MALE INFERTILITY

(75) Inventors: Susan Benoff, Riverdale, NY (US); Ian R. Hurley, Riverdale, NY (US); Robert G. Pergolizzi, New Milford, NY (US); Leslie Goodwin, Hicksville, NY (US)

(73) Assignee: North Shore - Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 09/970,882

(22) Filed: Oct. 5, 2001

Related U.S. Application Data

(60) Provisional application No. 60/281,830, filed on Oct. 5, 2000.

(51) Int. Cl.[7] ................................................ C12Q 1/68
(52) U.S. Cl. ......................... 435/6; 435/91.2; 536/23.1
(58) Field of Search ..................... 435/6, 91.2; 536/23.1

(56) References Cited

PUBLICATIONS

Goodwin et al. Molecular Human Reproduction, vol. 6, No. 2, pp. 127–236, Feb. 2000, see especially p. 132.*

Backx, P.H. et al., "Molecular Localization of an Ion–Binding Site Within the Pore of Mammalian Sodium Channels"; Science, Jul. 10, 1992, vol. 257, pp. 248–251.

Doyle, D. A. et al., "The Structure of the Potassium Channel: Molecular Basis of K+ Conduction and Selectivity"; Science, Apr. 3, 1998, vol. 280, pp. 69–77.

Catterall, W.A., "Structure and Function of Voltage–Gated Ion Channels"; Annu. Rev. Biochem., 1995, vol. 64, pp. 493–531.

Heinemann, S.H. et al., "Calcium channel characteristics conferred on the sodium channel by single mutations"; Nature, Apr. 2, 1992, vol. 356, pp. 441–443.

Satin, J. et al., "A Mutant of TTX–Resistant Cardiac Sodium Channels with TTX–Sensitive Properties"; Science, May 22, 1992, vol. 256, pp. 1202–1205.

Tanabe, T. et al., "Repeat I of the dihydropryridine receptor is critical in determining calcium channel activation kinetics"; Nature, Aug. 29, 1991, vol. 352, pp. 800–803.

Yang, J. et al., "Molecular determinants of Ca2+ selectivity and ion permeation in L–type Ca2+ channels"; Nature, Nov. 11, 1993, vol. 366, pp. 158–161.

Zhang, J–F. et al., "Molecular determinants of voltage–dependent inactivation in calcium channels"; Nature, Nov. 3, 1994, vol. 372, pp. 97–100.

* cited by examiner

Primary Examiner—Jeffrey Fredman
Assistant Examiner—Juliet C. Switzer
(74) Attorney, Agent, or Firm—Amster, Rothstein & Ebenstein LLP

(57) ABSTRACT

The present invention provides a method, oligonucleotide probes and primers, and assay kits for diagnosing an individual as having hypospermatogenesis associated infertility that involves demonstrating in the individual the presence or absence of a variant form of a gene in exons 6, 7, 8 or 9 of the L-VDCC α1c transcript.

22 Claims, 12 Drawing Sheets

Table 1
Catalog of individual splicing variants of the human testis α1c subunit

| Segment | Exon | Tissue-specificity | Number of clones |
|---|---|---|---|
| Amino terminus | 1 | Cardiac | 0/20 |
| | 1A | Testis(Fibroblast) | 20/20 |
| IS6 | 8 | Cardiac | 15/16 |
| | 8A | Testis(Fibroblast) | 1/16 |
| IIIS2 | 21 | Cardiac | 2/16 |
| | 22 | Testis | 13/16 |
| | 21 + 22 | Cardiac/Testis(Fibroblast) | 1/16 |
| IVS3 + linker | 31 + 33 | Testis(Fibroblast) | 36/50 |
| | 32 + 33 | Cardiac | 3/50 |
| | 31 + 32 + 33 | Testis(Fibroblast)/Cardiac | 2/50 |
| IVS3 w/o linker | 31 | Testis(Fibroblast) | 5/50 |
| | 32 | Cardiac | 3/50 |
| | 31 + 32 | Testis(Fibroblast)/Cardiac | 1/50 |

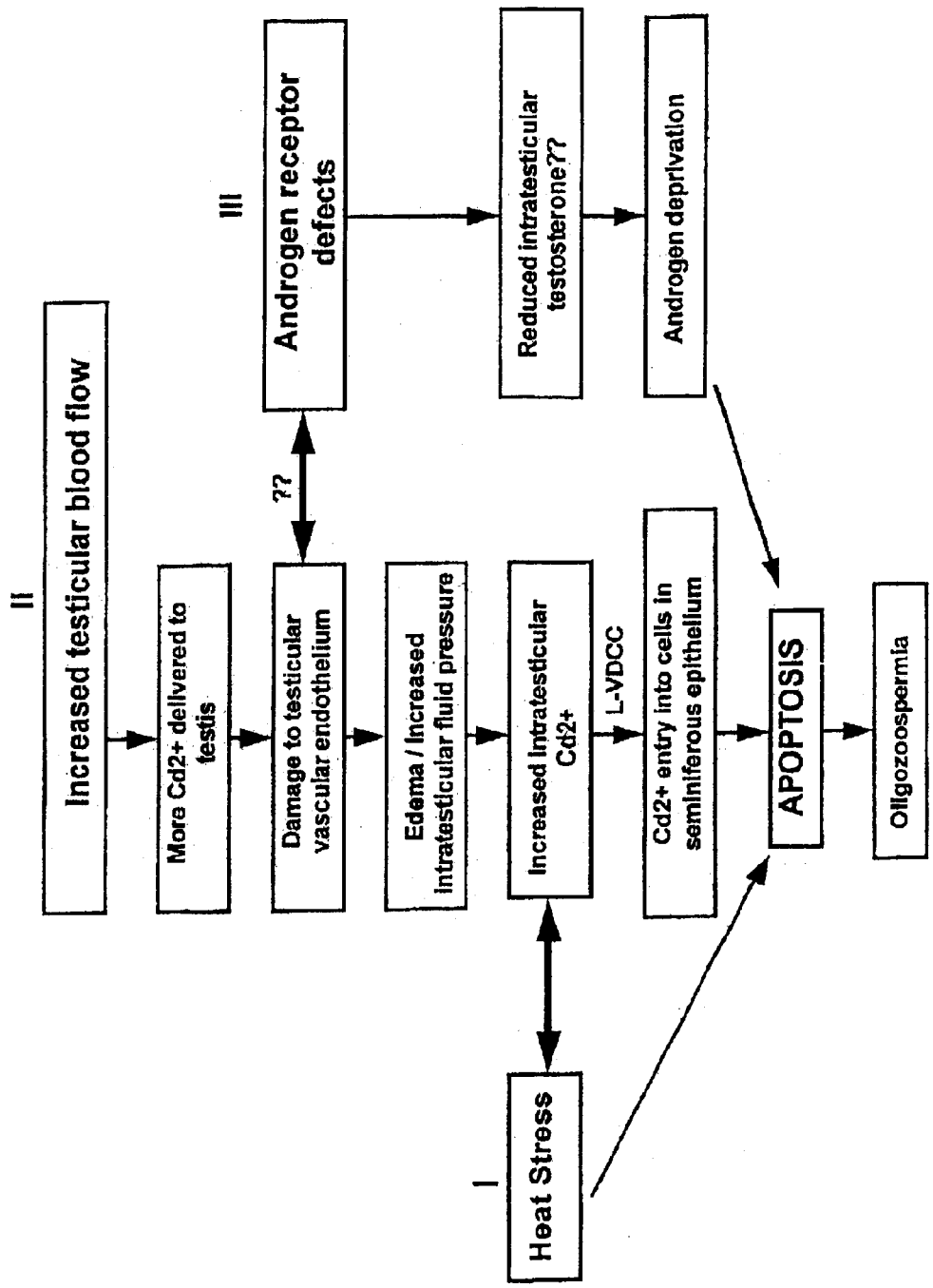

SEQUENCE LISTING

<160> NUMBER OF SEQ ID NOS: 16

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 1
ggtcctgaat tccatcatca aggccat

```
<210> SEQ ID NO 2
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 2
atcctcttct agctgctgcc ttctcc                                          26

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 3
tgacacgatc ttcaccaacc tgatcct                                         27

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 4
cacgatcagg agggccacat agggca                                          26

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 5
ggtcatccct gagctgaacg                                                 20

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 6
tccgttgtca taccaggaaa t                                               21

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 7
catagcagat gttccagcag                                                 20

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide probe
```

```
<400> SEQUENCE: 8
gtcatcttct gcttggaaca t                                      21

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 9
ggcatagcag atgacccttc c                                      21

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 10
actgggtcaa tgatgccgta g                                      21

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 11
gtaacaaaat agatccaggg c                                      21

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 12
aggacgctat gggctatgag                                        20

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 13
caggagggca tagcaaggac g                                      21

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 14
ggcatagcag gagagttttc c                                      21

<210> SEQ ID NO 15
<211> LENGTH: 21
```

-continued

```
<212> TYPE: DNA
<213> ORGANISM: Artificial Sequence
<220> FEATURE:
<223> OTHER INFORMATION: Oligonucleotide probe

<400> SEQUENCE: 15
gacgtgctgt actggggaga g                                              21

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide probe

<400> SEQUENCE: 16
acacgaatcg cctctcaaaa gg                                             22
```

OLIGONUCLEOTIDES FOR DETECTING MALE INFERTILITY

CROSS-REFERENCE TO RELATED APPLICATIONS

This application makes reference to U.S Provisional Patent Application No. 60/281,830 entitled "OLIGONUCLEOTIDE PROBES, ASSAYS AND KITS FOR VARICOCELE ASSOCIATED INFERTILITY," filed Oct. 5, 2000, the entire disclosure and contents of which is hereby incorporated by reference.

GOVERNMENT INTEREST STATEMENT

This invention is made with government support under Grant Nos. ES 06100 and ES 10496 to S.B. from the National Institute of Environmental Health Sciences, National Institutes of Health, Bethesda, Md. and, in part, by funds from the Division of Molecular Genetics, Department of Research, North Shore University Hospital. The government may have certain rights in this invention.

BACKGROUND OF THE INVENTION

1. Field of the Invention

The present invention relates to probes, assays and kits for diagnosing infertility in men.

2. Description of the Prior Art

In the medical study and practice of human reproduction, infertility is usually defined as the inability to conceive after 1 year of trying. The term infertility is not the same as sterility, since many couples ultimately may achieve a pregnancy after 1 year of unprotected intercourse. Over 4.5 million American men and women—or roughly 1 out of 5 (15–20%) couples—fail when attempting their first pregnancy. In these couples, about half of the men will have a significant abnormality that makes them unable to father children. Male infertility may be caused by abnormalities in the testes or other areas of the male reproductive tract, as well as immune system defects. Yet the most common cause of male infertility is disordered sperm production. Other medical conditions that could cause infertility include a varicocele, abnormalities of the testes, penis, prostate or secondary sex traits.

Four main factors govern male fertility: hormones, sperm production, the ductal system of sperm delivery, and sexual function. Among these factors, physical variables that affect the structure of the testes are particularly important. There are many types of male infertility with a variety of causes and results.

"Varicocele" describes dilated internal spermatic veins forming the pampiniform plexus. This dilation results from increased intra-abdominal and hydrostatic pressures transmitted to the internal spermatic veins. Varicoceles have been associated with a common type of male infertility in which there is loss of ipsilateral testicular volume, oligozoospermia with increased numbers of sperm with a tapered head shape ("stress pattern"), impaired sperm motility and a reduced ability to undergo an acrosome reaction.

Approximately 40% of males from infertile couples present with varicocele. The mechanism(s) underlying the production of infertility with varicocele, however, are poorly characterized. The most widely accepted explanation for the pathophysiology of varicocele in male infertility is abnormally elevated testicular temperature due to impaired heat transfer by the scrotum and/or changes in testicular blood flow. Although men with varicocele exhibit higher mean scrotal temperatures, there is a large overlap with the range of scrotal temperatures in fertile men. More importantly, only 13% of men with varicocele are infertile, and, although varicocele repair has been documented 30 to reduce testicular temperature, only ⅓ of infertile men with varicocele-associated infertility will experience a return of fecundity following varicocele correction. These findings suggest that varicocele may not be a primary cause of infertility and that it is the interaction of varicocele with other factors that produces the infertile state.

Other etiologies of human male infertility include such conditions as cryptorchidism, retrograde ejaculation, testicular tumor, endocrine disorders, Kallmann's syndrome, fertile eunuch syndrome, congenital adrenal hyperplasia, Prader-Willi syndrome, Lawrence-Moon-Biedl syndrome, hemochromatosis, primary hypogonadism, Klinefelter's syndrome, XX disorder, XYY syndrome, mixed gonadal dysgenesis, Noonan syndrome, Myotonic dystrophy, 5-alpha-reductase deficiency, androgen receptor deficiency, among other known conditions.

SUMMARY OF THE INVENTION

It is therefore an object of the present invention to provide oligonucleotide probes for determining hyposperrnatogenesis associated infertility.

It is therefore an object of the present invention to provide oligonucleotide probes for determining varicocele associated infertility.

It is another object of the present invention to provide assays for determining hypospermatogenesis associated infertility.

It is another object of the present invention to provide assays for determining varicocele associated infertility.

It is yet another object of the present invention to provide kits for determining hypospermatogenesis associated infertility.

It is yet another object of the present invention to provide kits for determining varicocele associated infertility.

According to first broad aspect of the present invention, there is provided a method for diagnosing an individual as having hyspernatogenesis or varicocele associated infertility, which comprises demonstrating in the individual the presence or absence of a variant form of a gene in exons 6, 7, 8 or 9 of the L-VDCC α1c transcript.

According to a second broad aspect of the present invention, there is provided an ligonucleotide hybridization probe for diagnosing an individual as having infertility or a predisposition thereto, which probe comprises a sequence of nucleotides such that under suitably stringent conditions the probe specifically binds to a variant form of a gene in exons 6, 7, 8 or 9 of the L-VDCC α1c transcript; and fails to show significant hybridization to genetic material derived from individuals lacking said variant form of said gene.

According to a third broad aspect of the present invention, there is provided an oligonucleotide primer selected from the group of primers consisting of SEQ ID NO: 1, SEQ ID NO: 2, SEQ ID NO: 3, and SEQ ID NO: 4.

According to a fourth broad aspect of the present invention, there is provided an assay kit which comprises an oligonucleotide hybridization probe for diagnosing an individual as having infertility or a predisposition thereto, which probe comprises a sequence of nucleotides such that under suitably stringent conditions the probe specifically binds to a variant form of a gene in exons 6, 7, 8 or 9 of the LVDCC α1c transcript; and fails to show significant hybridization to genetic material derived from individuals lacking said variant form of said gene.

According to a fifth broad aspect of the present invention, there is provided an assay kit that comprises an oligonucleotide primer selected from the group of primers consisting of SEQ ID NO: 1, SEQ ID NO: 2, SEQ ID NO: 3, and SEQ ID NO: 4.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 1A is a deduced consensus amino acid sequence of testis specific L-VDCC α1C subunit;

FIG. 1B is a table cataloging individual splicing variants of the human testis α1C subunit;

FIG. 10 illustrates a proposed model for multifactorial etiology of apoptosis leading to oligozoospermia in varicocele-associated infertility.

DETAILED DESCRIPTION OF THE PREFERRED EMBODIMENT

Definitions

Figure 2A:
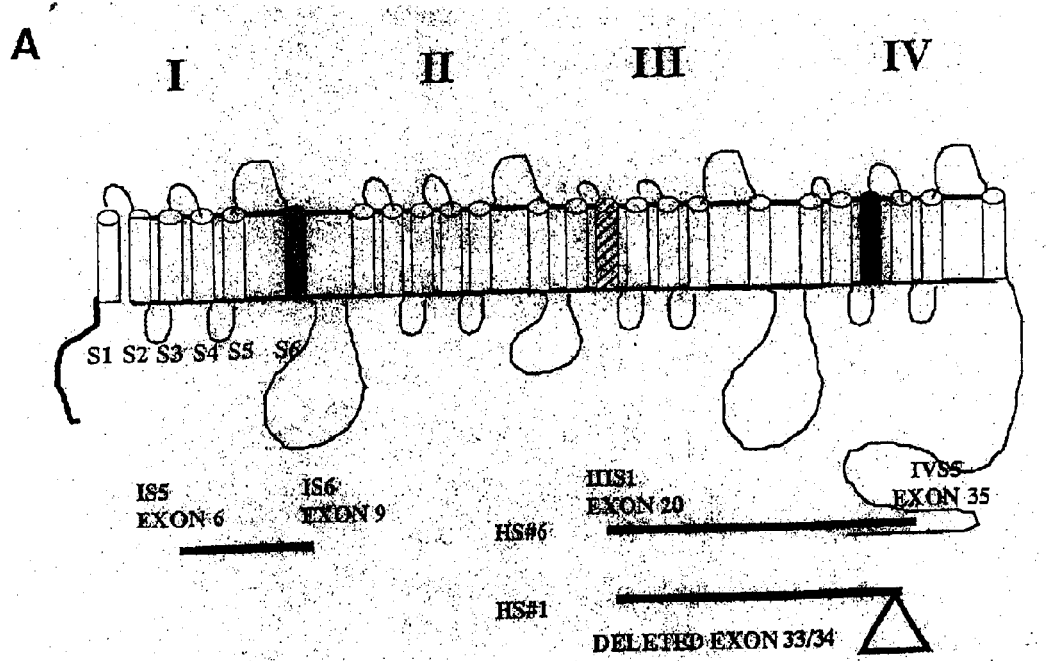
FIG. 2A illustrates the identification of structure function relationships for the human spenn L-VDCC α1C subunit.

It is advantageous to define several terms before describing the invention. It should be appreciated that the following definitions are used throughout this application.

For the purposes of the present invention, the term "spermatogenesis" refers to a hormonally regulated process where germ cells differentiate into mature spermatozoa by passing through several stages of meiosis. These intervening stages are of spermatogonia type A and B, primary spermatocytes that undergo meiosis to form two secondary spermatocytes, secondary spermatocytes undergo second meiotic division to form two sperm atids, and spermnatids finally transform into spermatozoa.

For the purposes of the present invention, the term "hypospermatogenesis" refers to a reduction in quantitative spennatogenesis throughout the testis.

Description

In general, male infertility may be caused by abnormalities in the testes or other areas of the male reproductive tract, as well as immune system defects. The most common cause of male infertility is disordered sperm production. Other medical conditions that could cause infertility include a varicocele, abnormalities of the testes, penis, prostate or secondary sex traits.

Four main factors govern male fertility: hormones, sperm production, the ductal system of sperm delivery, and sexual function. Among these factors, physical variables that affect the structure of the testes are particularly important. There are many types of male infertility with a variety of causes and results.

A condition common to many types of male infertility is hypospertnatogenesis. Hypospermatogenesis refers to a reduction in quantitative spermatogenesis throughout the testis. This condition may result from a variety of causes.

One cause of hypospermatogenesis is varicocele. "Varicocele" describes dilated internal spermatic veins forming the pampiniform plexus. This dilation results from increased intra-abdominal and hydrostatic pressures transmitted to the internal spermatic veins. Varicoceles have also been associated with a common type of male infertility resulting from hypospermatogenesis in which there is loss of ipsilateral testicular volume, oligozoospermia with increased numbers of sperm with a tapered head shape ("stress pattern"), impaired sperm motility and a reduced ability to undergo an acrosome reaction.

Approximately 40% of males from infertile couples present with varicocele. The mechanism(s) underlying the production of infertility with varicocele, however, are poorly characterized. The most widely accepted explanation for the pathophysiology of varicocele in male infertility is abnormally elevated testicular temperature due to impaired heat transfer by the scrotum and/or changes in testicular blood flow. Although men with varicocele exhibit higher mean scrotal temperatures, there is a large overlap with the range of scrotal temperatures in fertile men. More importantly, only 13% of men with varicocele are infertile, and, although varicocele repair has been documented to reduce testicular temperature, only ⅓ of infertile men with varicocele-associated infertility will experience a return of fecundity following varicocele correction. These findings suggest that varicocele may not be a primary cause of infertility and that it is the interaction of varicocele with other as yet unidentified factors that produces the infertile state.

Y chromosome microdeletions can produce oligozoospermia, but only about 3% of men with varicocele have detectable deletions. Thus, there must be other ancillary factors operating. Preliminary findings indicate that the fraction of apoptotic germ cells in the seminiferous epithelium and in the ejaculate of infertile men with varicocele is significantly higher than in normal fertil men. Apoptotic cell death is an essential process in normal spermatogenesis, being regulated by gonadotrophins and androgens. Increased apoptotic frequency has been reported in a variety of hypospermatogenic states. Therefore, the critical ancillary factors may regulate apoptosis.

In a search for these factors, three sets of observations were analyzed. First, cigarette smoke increases impairment of spermatogenesis in men with varicocele and in animal varicocele models. Second, actin filaments regulate spermiation and shape of sperm heads; actin polymerization and depolymerization is also required in order to effect acrosome exocytosis. Third, actin loss increases apoptosis in somatic cells.

Cigarette smoke is rich in toxic metal ions. Each cigarette contains 0.6–2.0 $\mu$g lead ($Pb^{2+}$) and 1–4.5 $\mu$g cadmium ($Cd^{2+}$), and at least one tenth of the metal content of a cigarette is inhaled. Testicular apoptosis can be increased by elevated temperature, as observed in varicocele, and by elevated $Cd^{2+}$ levels. Both heat and $Cd^{2+}$ can also degrade actin filaments. Therefore, an interaction between elevated scrotal temperature with varicocele and $Cd^{2+}$ may result in the production of an infertile state. This suggestion was strongly supported by subsequent experimental findings.

The levels and distributions of $Cd^{2+}$ in blood plasma, seminal plasma and testis biopsies from men with and without varicocele-associated infertility who did not smoke cigarettes were compared. Although blood plasma $Cd^{2+}$ levels were similar in infertile men with varicocele and in controls (fertile men without varicocele, fertile men with varicocele, infertile men without varicocele), both testicular and seminal plasma $Cd^{2+}$ levels were elevated only in infertile men with varicocele. The increase in $Cd^{2+}$ content in specimens from infertile men with varicocele was associated with loss of actin from both seminiferous tubules and the mature sperm head as well as increased apoptosis in the germinal epithelium. Results from in vitro modeling studies support the in vivo findings. Exogenous $Cd^{2+}$ exposure produced changes in fertile donor sperm protein expression (e.g., loss of sperm head actin) and function (e.g., an acrosome reaction insufficiency) that mimic those of varicocele-associated infertility, albeit at 30-fold higher $Cd^{2+}$ levels than found in seminal plasma from infertile men with varicocele. Importantly, however, when fertile donor sperm were briefly exposed to higher temperatures, lower exogenous $Cd^{2+}$ levels produced more drastic loss of sperm function, indicating that, as observed in cryptorchid animal models in vivo, the effects of temperature and $Cd^{2+}$ are synergistic.

Data indicates that men with varicocele-associated infertility are more sensitive ("susceptible") than the general population to environmental $Cd^{2+}$ exposures. This may be considered analogous to findings in animals that sensitivity to $Cd^{2+}$ differs among mouse and rat strains. In men with varicocele, this susceptibility may result from increased venous pressure (increasing microvasculature fluid exchange and flux of $Cd^{2+}$ from blood plasma through the blood/testis barrier and the fact that tissue $Cd^{2+}$ levels are not homeostatically controlled (i.e., there is no active $Cd^{2+}$ clearance pathway, see FIG. 10).

However, it is recognized that $Cd^{2+}$ must enter cells in the seminiferous epithelium, possibly via L-VDCC, in order to disrupt actin filaments, alter spermatogenesis and reduce sperm production and acrosome response. L-VDCC are expressed in Sertoli cells and all cells of the male germ cell lineage, from Type A spermatogonia to mature sperm. L-VDCC have previously been shown to be incompletely specific, being able to pass $Cd^{2+}$, $Pb^{2+}$, zinc, nickel, cobalt, aluminum and manganese in addition to $Ca^{2+}$ in both somatic cells and in mammalian sperm. Nifedipine, a potent dihydropyridine blocker of L-VDCC that produces a reversible male infertile state, has been demonstrated to block $Cd^{2+}$-induced toxicity in mouse pre-implantation embryos by inhibiting intracellular $Cd^{2+}$ accumulation. Dihydropyridines and other classes of L-VDCC blockers also inhibit $Cd^{2+}$ uptake by somatic cells.

It is well known that the effects of metal ions on LVDCC differ among cell types and among channel subtypes. It is also recognized that single amino acid changes alter the ion-selection properties of voltage-gated channels. Distinct binding sites for $Pb^{2+}$, $Cd^{2+}$ and other metal ions appear to regulate ion permeation. It is therefore important to note that $Ca^{2+}$ channel polymorphisms are associated with the production of disease states. Based on these findings, L-VDCC isoform expression may be a genetic co-factor mediating $Cd^{2+}$ effects in human testis.

$Cd^{2+}$ and other metal ions may enter the human sperm head through L-VDCC. The present invention provides the first complete sequence for an L-VDCC α1C subunit expressed in human testis and sperm. Multiple isoforms of this subunit are produced by alternative splicing of a single mRNA transcript and preliminary findings suggest that structural changes may be associated with alterations in the ability of human sperm to undergo a zona pellucida-induced acrosome reaction. Finally, the variable expression of a region of the L-VDCC α1C subunit that potentially regulates sensitivity or resistance to $Cd^{2+}$ is characterized herein. Initial observations suggest alterations in this region of the α1C structure are associated with hypospermatogenic states.

The present invention provides methods, hybridization probes and primers, and assay kits for diagnosing an individual as having hypospennatogenesis associated infertility, which involve demonstrating that the individual has a variant form of a gene in exons 6, 7, 8 or 9 of the L-VDCC α1c transcript. The method of the present invention may employ conventional means for testing for variant genes such as adhering hybridization probes for the normal gene and one or more types of hybridization probes for the variant gene on a substrate, such as a silicon chip forming a so-called oligo-chip. Other methods of testing for genetic variants that may be adapted for use in the method of the present invention are described in U.S. Pat. Nos. 6,100,027; 6,103,476; 6,110,670; 6,110,681; 6,114,151; 6,203,989; 6,228,575; 6,238,862; and 6,261,776, the entire contents and disclosures of which are hereby incorporated by reference. Methods of the present invention may also employ an indirect detection mechanism through the use of an amplification system utilizing, for example, anti-biotin antibodies and anti-antibodies. Such a mechanism may increase the sensitivity of the diagnosis.

Methods that may be adapted for use in forming the oligonucleotide probes of the present invention are described in U.S. Pat. Nos. 6,100,027; 6,103,476; 6,110,670; 6,110,681; and 6,114,151, the entire contents and disclosures of which are hereby incorporated by reference.

Methods that may be adapted for use in forming the assay kits of the present invention are described in U.S. Pat. Nos. 6,100,027; 6,103,476; 6,110,670; 6,110,681; and 6,114,151, the entire contents and disclosures of which are hereby incorporated by reference.

Hybridization probes of the present invention may be made from DNA, RNA, or some combination of the two.

The probes may include modified nucleotides. Modified internucleotide linkages are useful in probes comprising deoxyribonucleotides and ribonucleotides to alter, for example, hybridization strength and resistance to non-specific degradation and nucleases. The links between nucleotides in the probes may include bonds other than phosphodiester bonds, for example, peptide bonds. Modified internucleotide linkages are well known in the art and include methylphosphonates, phosphorotlioates, phosphorodithionates, phosphoroamidites and phosphate ester linkages. Dephospho-linkages are also known, as bridges, between nucleotides and include siloxane, carbonate, carboxymethyl ester, acetamidate, carbamate, and thioether bridges. "Plastic DNA," having for example N-vinyl, methacryloxyethyl, methacrylatiide or ethylene-imine internucleotide linkages can also be used in probes (see e.g. Uhlmann and Peyman (1990) pp. 545–569) "Peptide Nucleic Acid" (PNA), the entire contents and disclosure of which is hereby incorporated by reference) is particularly useful because of its resistance to degradation by nucleases and because it forms a stronger hybrid with natural nucleic acids. (Orum et al. (1993); Egholm, et al. (1993), the entire contents and disclosure of which is hereby incorporated by reference).

Exemplary probes of the present invention are including in the following list. The probes are included in the Sequence Listing as SEQ ID NOS: 7–16, listed from top to bottom.

| Detection Region | Probe Sequence | Melting Temperature |
| --- | --- | --- |
| HT1/1' - Normal exon 6 | 5' CATAGCAGATGTTCCAGCAG | 57.0° C. |
| HT1/1' - Normal exon 7 | 5' GTCATCTTCTGCTTGGAACAT | 56.8° C. |
| HT2 - 16 bp deletion at beginning of exon 7 | 5' GGCATAGCAGATGACCCTTCC | 63.1° C. |
| HT1 - Normal exon 7/8 | 5' ACTGGGTCAATGATGCCGTAG | 58.0° C. |
| HT1 - Normal exon 8 (fibroblast) | 5' GTAACAAAATAGATCCAGGGC | 46.8° C. |
| HT1' - Exon 8 (cardiac) | 5' AGGACGCTATGGGCTATGAG | 59.3° C. |
| HT4 - Exon 7 deletion | 5' CAGGAGGGCATAGCAAGGACG | 66.3° C. |
| HT5 - Exon 7 and 8 deletion | 5' GGCATAGCAGGAGAGTTTTCC | 60.2° C. |
| HT3 - Exon 8 deletion | 5' GACGTGCTGTACTGGGGAGAG | 62.2° C. |
| HT1/1' - Normal exon 9 | 5' ACACGAATCGCCTCTCAAAAGG | 64.8° C. |

In preferred embodiments of the present invention, suilably stnngcnt conditions should be of a highly stringent nature to ensure the elimination of false positives, such that (as with the Affmetrix chips) a single nucleotide mismatch in the center of the probe will be sufficient to prevent hybridization. The precise hybridization conditions of the final reaction of biological samples with the oligonucleotides, present for example on oligo-chips, will, however, vary depending on the length of the oligonucleotides ultimately chosen as probes and their GC content as well as on the source of the test RNA population. Therefore, hybridization conditions can vary between 42° C. and 60° C. for approximately 16 hours. In certain embodiments, the present invention may use hybridization conditions that are <10° C. below the calculated melting temperature ($T_m$) of the perfect hybrid. Salt concentration and source also affect the hybridization conditions, i.e., whether sodium chloride or quaternary alkylamnronium salts are employed. Stringency is also affected by post-hybridization washes and will vary based on rapidity of washing and on salt concentration and temperature employed (e.g., low stringency [1×SSC/0.1% SDS/45° C.] vs. moderate stringency [0.1×SSC/0.1% SDS/45° C.] vs. high stringency [0.1×SSC/0.1% SDS/60° C.]). The exact hybridization conditions may be adjusted according to one of ordinary skill in the art based on the disclosure of the present invention.

The present invention will now be described by way of exanple

EXAMPLE

Ezxample 1

Prior studies showed $Cd^{2+}$ levels in testis biopsies (TB; n=21 (where n=number of samples analyzed)) and seminal plasma (SP; n=65) from varicocele associated infertility (VAI) affected men was markedly increased when compared to cadmium ($Cd^{2+}$) levels in TB (n=14) and SP (n=99) from fertile men (P<0.0001). The "P" value was determined using an Analysis of Variance (ANOVA) model. VAI TB increased $Cd^{2+}$ levels were associated with decreased actin imiunostaining and increased germ cell apoptosis (P<0.001), and reduced pregnancy rates after varicocele repair (P<0.007). Exposure of fertile donor sperm (n=9) to exogenous $Cd^{2+}$ caused loss of sperm head actin (P<0.0001) and an acrosome reaction insufficiency (P<0.007), mimicking that in VAI. These in vitro studies revealed that sites of sperm head $Cd^{2+}$ entry colocalized with ion pore-forming α1 subunit of L-type voltage dependent ion channels that normally transport calcium ($Ca^{2+}$)(L-VDCC), which is also expressed in the germinal epithelium. The typical L-VDCC α1 subunit is comprised of 4 repetitive domains (I–IV), each containing 6 putative transmembrane segments (S1–S6). Somatic variants may transport $Cd^{2+}$ in addition to $Ca^{2+}$. Multiple (12–16) human testis- and sperm-specific LVDCC α1 isoforms are produced by alternative splicing of the primary transcript from the same gene that encodes the cardiac L-VDCC. Testis/sperm L-VDCC α1 subunits differ from the cardiac in four regions, including IS6 that is encoded by exons 8 and 8A. IS6 is responsible for both channel inactivation kinetics and sensitivity or resistance to $Cd^{2+}$. The deleterious effects of increased VAI $Cd^{2+}$ may correlate with particular L-VDCC α1 isoforms varying in this region. The purpose of this study was to develop a reliable assay for identification of expression of exon 8 or 8A in testis/sperm L-VDCC α1 transcripts, in preparation for a large prospective VAI study.

Example 2

Design.

Potential diversity in L-VDCC α1 transcripts was examined in pooled samples of mRNA from human testis (n=20) and individual isolates of RNA from ejaculated motile sperm of normospermic donors (n=8) through reverse transcription-polymerase chain reaction (RT-PCR) amplifications of exons 6–9 (transmembrane regions IS5–IS6 and the cytoplasmic linker between domains I–II).

Materials and Methods.

Under an Institutional Review Board (IRB) dpproved protocol, total RNA was extracted from individual human sperm populations (~4×10⁷ sperm) using SDS/citric acid and alcohol precipitation. PCR products generated from sperm RNA templates and human testis MRNA template (Clontech) were gel purified before sequencing. The MacVector 5.0 program was used for sequence alignments.

Products and Reagents.

Modified Ham's F-10 medium without hypoxanthine (Catalog No. 9461) was obtained from Irvine Scientific (Santa Anna, Calif.). Optima grade (trace metal ion free) concentrated hydrochloric and nitric acids were obtained from Fisher Scientific Company (Pittsburgh, Pa.). All polymerase chain reaction (PCR) reagents were purchased from Perkin-Elmer (Foster City, Calif.). All other enzymes were obtained from New England Biolabs (Beverly, Mass.). Unless otherwise noted, all other reagents were purchased from Sigma Chemical Company (St. Louis, Mo.).

Human Subjects.

All protocols employing human subjects were reviewed and approved by the Institutional Review Board of North Shore University Hospital.

Semen donors of known fertility participated after giving written informed consent. All testicular and prostatic biopsies were obtained at the time of varicocele repair or other clinically dictated procedures and were obtained as pathological specimens at point of discard. No patient underwent a biopsy solely for research purposes.

Semen Analysis and Preparation.

Semen specimens from number coded fertile donors were collected by masturbation and allowed to liquefy for up to one hour after collection. Smears prepared from raw semen were air dried, stained with Stat III Andrology Stain (Mid-Atlantic Diagnostics, Inc., Medford, N.J.), and evaluated for the incidence of immature forms (as indicated by the presence of residual cytoplasm in the sperm head-neck region).

Only specimens with the following characteristics were used in these studies: >50×$10^6$ sperm/mL, >50% motility, and >10% normal forms, as determined by morphologic evaluation using strict criteria Motile sperm populations were recovered from fresh semen by swim-up. Highly motile populations were routinely obtained: 99.0±3.9%.

Localization of Human Sperm L-VDCC.

The topographical distribution of LVDCC on the human sperm plasma membrane was examined by indirect immunocytochemistry as previously described Benoff, "Carbohydrates and fertilization: an overview" in *Mol. Hum. Reprod.* 1997b, 3:599–637, the entire contents and disclosure of which is hereby incorporated by reference. Control reactions were performed with rabbit polyclonal sera against muscle actin (Sigma No. A-2668).

Autometallography.

To study sites of exogenous metal ion entry into human sperm, motile sperm populations from fertile donors were incubated overnight at 37° C. in 5% $CO_2$ in capacitation media (Ham's F-10+30 mg/ml charcoal-delipidated human serum albumin (HSA)) supplemented with 146 µg/L $Cd^{2+}$ or with 22 mM zinc ($Zn^{2+}$). Sperm were washed free of exogenous metal ions and sperm-bound metals were detected by autometallography. Specifically, the protocol used to demonstrate the topographical association between metal ions and rat and human sperm and provided by the originator, Dr. Meredin Stoltenberg (Institute of Anatomy, University of Aarhus, Denmark) was employed. This is a highly sensitive technique; after conversion to metal sulfides by reaction with sodium sulfide, <10 catalytic atoms of a given metal can be visualized as black silver deposits ("BSDs") by physical development with silver lactate.

Although different metals produce different shaped BSDs, the present invention shows the localization of $Cd^{2+}$ and $Zn^{2+}$ chemically. After development, one slide that had previously been treated with sodium sulfide was incubated in 0.1 N HCl/1% KCN for 1 hour at room temperature. This treatment dissolved BSDs resulting from $Zn^{2+}$. A second slide that had previously been treated with sodium sulfide was incubated in 1% $H_2O_2$ for 1 hour at room temperature. This oxidation eliminated BSDs resulting from $Cd^{2+}$ sulfides.

Induction of the Acrosome Reaction.

Motile human sperm populations were incubated overnight under sperm capacitating conditions (see above). Acrosome exocytosis was induced by sperm exposure to 100 µg/mL mannosylated-BSA (Sigma No. A7790) in the presence of 75 mM D-mannose monosaccharide. Control aliquots were exposed to mannosylated-BSA alone. Acrosome-intact and acrosome-reacted sperm were differentiated by reaction with 100 µg/mL rhodamine-labeled *Pisum sativum* agglutinin ("RITC-PSA"; Vector Laboratories, Inc., Burlingame, Calif.).

Testis Biopsies.

All subjects were non-smokers. A complete medical history, including occupational exposures and a drug/medication profile, was obtained for all males evaluated for primary infertility and a comprehensive multisystem physical examination was performed. Enrolled patients had two naturally descended testes and no other known systemic medical illness. Testicular size was measured by ultrasound (Hitachi 515a; 7.5 MHz linear array probe) for each patient. Using these measurements, testicular volume was calculated by approximation to a prolate ellipsoid (0.54.length.width.height). Doppler flow ultrasound was used to determine varicocele size. A varicocele was defined as veins with >3.0 mm diameter measured posterior to the testis, midway on an axial projection with a reversal of flow noted by flow ultrasound.

Testicular tissue was obtained by the percutaneous needle aspiration biopsy technique developed by Marmar. All biopsy material was immediately fixed in it formalin. Although Bouins fixative better preserves testicular architecture, formalin was chosen as fixative as it both preserves the antigenic character of the tissue and anl inactivates RNases.

A portion of each fixed specimen was processed, embedded in paraffin and sectioned. Testis sections (9 µm) were collected on adhesive pre-treated slides (in situ PCR glass slide; Perkin-Elmer, Foster City, Calif., USA), deparaffinized in xylene, rehydrated in ethanol-water mixtures and baked at 60° C. for 1 hour. The Johnsen scoring system was used to assess spermatogenesis in hematoxylin and eosin stained biopsy sections.

Analysis of Apoptosis.

Apoptosis in testis biopsy sections was quantified in situ by deoxynucleotidyl transferase labeling (TUNEL). All TUNEL assays were performed using TACS 2 TdT-DAB In Situ Apoptosis Detection Kit (Catalog No. 4810-30-K; Trevigen, Inc., Gaithersburg, Md., USA) according to the manufacturer's protocol.

Determination of Testicular $Cdz^{2+}$ Levels by Graphite Furnace Atomic Absorption Spectroscopy, All plasticware used in these experiments was soaked sequentially for 24 hours each in 20% hydrochloric acid and 20% nitric acid, washed 20 times with deionized $H_2O$ and stored in deionized $H_2O$ until use.

A portion of each testis or prostate biopsy was weighed and lyophilized until a constant reduced weight was obtained. The protein matrix in each sample was removed by digestion with concentrated nitric acid under high pressure in a microwave. The resulting aqueous supernatant solutions were assayed for $Cd^{2+}$ content at 228.8 nm wavelength in the presence of a matrix modifier (5000 μg/1 NH$_2$H$_2$PO$_4$) on a SpectrAA 250 Plus atomic absorption spectrometer equipped with a GTA 97 graphite furnace (Varian Instruments, Sugar Land, Tex.) using the method of standard additions to correct for matrix effects. Cd$^{2+}$ levels were quantified relative to 0.25 μg/L to 4.0 μg/L Cd$^{2+}$ standards (Inorganic Ventures, Inc., Lakewood, N.J.). The detection limit was 0.1 μg/L, i.e., three times the blank value. As a control, selected samples were spiked with varying amounts of Cd$^{2+}$. Cd$^{2+}$ levels matched within 5% of the expected values.

Distribution of Actin Epitopes in Testis Biopsies.

Testis sections were reacted with anti-actin antibodies (rabbit polyclonal sera against muscle actin; Sigma No. A-2668) following established laboratory protocols.

Isolation of RNA from human sperm.

RNA in freshly isolated motile sperm populations was extracted using reagents from a Purescript RNA Isolation Kit (Gentra Systems, Inc., Minneapolis, Minn.) and a protocol modified from that supplied by the manufacturer in that after addition of the "Cell Lysis" solution, dithiothreitol (DTT) was added to a final concentration of 40 mM and the mixture was incubated for 4 hours at 55° C. prior to addition of the "Protein-DNA Precipitation" solution. This improved the overall yield of RNA.

Human Testis Poly(A)+RNA.

Hunan testis poly(A)+RNA was purchased from Clontech (Palo Alto, Calif.). the RNA was purified using guanidinium isothiocyanate and oligo(dT)-cellulose columns. The preparation used was obtained from a pool composed of testis tissue from 20 men, aged 6 months to 70 years, and was checked for integrity on a denaturing agarose gel.

Isolation of RNA from Formalin-fixed Human Testis Biopsies.

RNA was isolated from portions of formalin-fixed human testis biopsies (7–22 mg) using a Purescript RNA Isolation kit and a protocol modified from that supplied by the manufacturer in that the pulverized tissue was incubated for 40 minutes in "Cell Lysis" solution, with or without subsequent glycogen precipitation of extracted RNA.

PCR Primers.

Figure 1A:
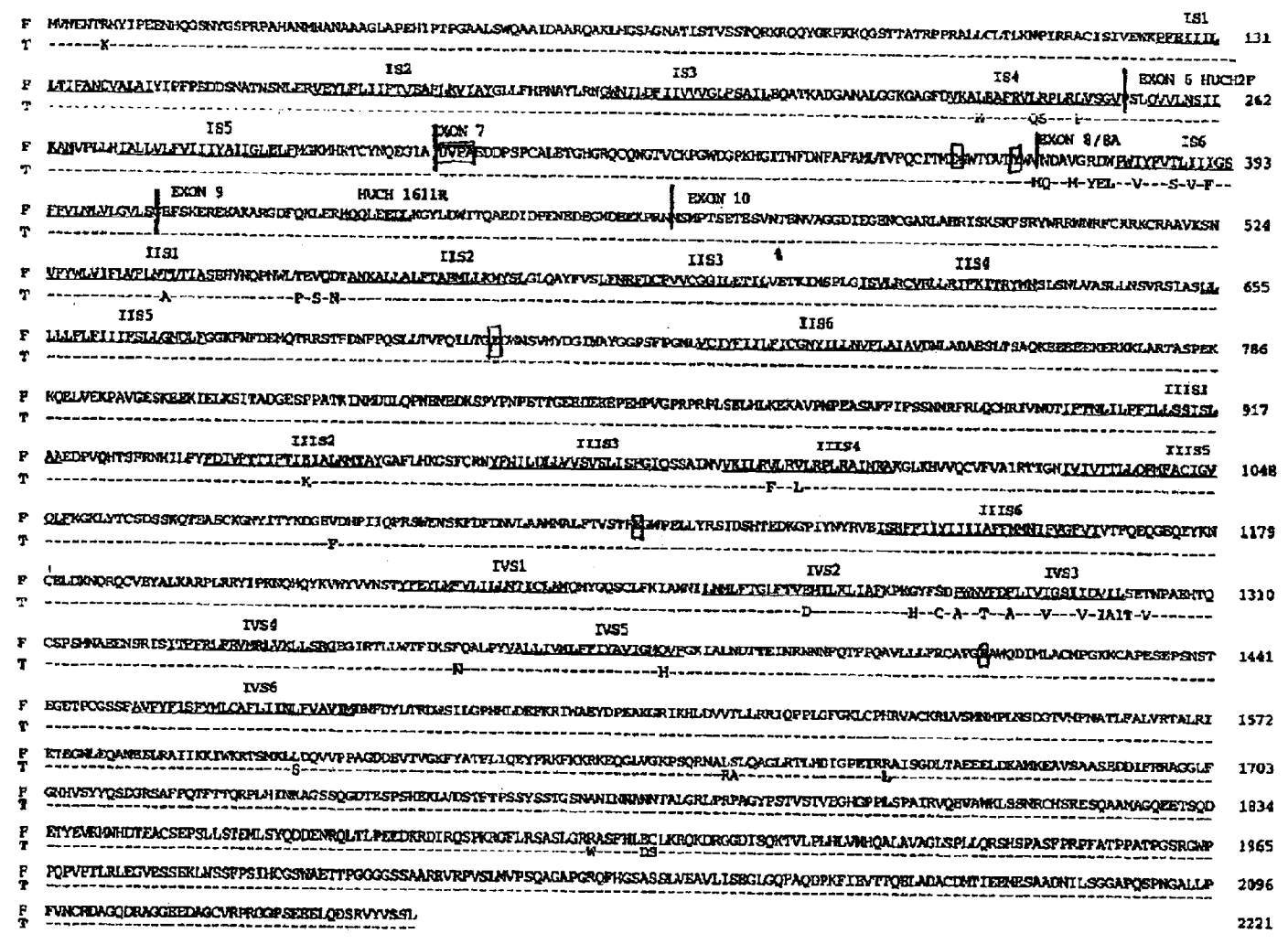

Oligonucleotide primers were synthesized on an Applied Biosystems Model 394 DNA Synthesizer (Foster City, Calif.). Sets of forward (F) and reverse (R) primers were designed to detect the alternatively spliced transmembrane segment IS6 (Table 1) and surrounding sequences (exons 6–9) in the L-VDCC α1C subunit (FIGS. 1 and 2A) (HUCH 2F (SEQ ID NO: 1) and HUCH 1611R (SEQ ID NO: 2)), to amplify L-VDCC α1C exons 20–35 which surround alternatively expressed transmembrane segments IIIS2 and IVS3 (Table 1; FIGS. 1 and 2A) (HUCH 3F2 (SEQ ID NO: 3) and HUCH 6R2 (SEQ ID NO: 4)), and to identify transcripts directing the synthesis of human glyceraldehyde-3-phosphate dehydrogenase [hGAPDH (HG 690F (SEQ ID NO: 5) and HG 984R (SEQ ID NO: 6))]. The hGAPDH primers employed were designed to amplify nucleotides 690–984 of the hGAPDH mRNA sequence (Accession No. M17851). The region is derived from exons 8 and 9 of the human GAPDH gene, which are separated in the genome by a 100 bp intron (Accession No. 104038).

| HUCH 2F | 5' GGTCCTGAATTCCATCATCAAGGCCAT | (SEQ ID NO: 1) |
|---|---|---|
| HUCH 1611R | 5' ATCCTCTTCTAGCTGCTGCCTTCTCC | (SEQ ID NO: 2) |
| HUCH 3F2 | 5' TGACACGATCTTCACCAACCTGATCCT | (SEQ ID NO: 3) |
| HUCH 6R2 | 5' CACGATCAGGAGGGCCACATAGGGCA | (SEQ ID NO: 4) |
| HG 690F | 5' GGTCATCCCTGAGCTGAACG | (SEQ ID NO: 5) |
| HG 984R | 5' TCCGTTGTCATACCAGGAAAT | (SEQ ID NO: 6) |

Primers of the present invention identified as SEQ ID NOS: 1–6 may be modified according to one of ordinary skill in the art in a manner that permits the primer to function. Such modifications include the addition of short nucleotide ends of 1–6 nucleotides at the 3' and/or 5' ends of the sequences. Typically, a primer sequence having at least 50%, preferably at least 70%, and even more preferably at least 90% homology to the primers identified in SEQ ID NOS: 1–6 may be utilized in the present invention.

Conditions for RT-PCR and DNA Sequence Analysis.

First strand cDNA was synthesized using a Reverse Transcription System kit (Promega, Madison, Wis.), concentrated by ethanol precipitation, and converted to double stranded cDNA and amplified using gene-specific primers. A two step amplification was employed for L-VDCC α1C primer pairs (HUCH 2F/HUCH1611R (SEQ ID NO: 1/SEQ ID NO: 2): 40 cycles at 94° C. for 30 seconds/72° C. for 1 minute; HUCH 3F2/HUCH 6R2 (SEQ ID NO: 3/SEQ ID NO: 4): 45 cycles at 94° C. for 30 seconds/72° C. for 4 minutes) while amplification with hGAPDH-specific primers required three steps (94° C. for 30 seconds/58° C. for 30 seconds/72° C. for 1 minute; 35 cycles). The size of the PCR products was estimated by co-electrophoresis of 1/10 (10 μL) of the completed PCR reaction and 500 ng of molecular weight size standards (1 Kb DNA ladder, Cat. no. 5615SB, Gibco-BRL, Grand Island, N.Y.) on a 1.2% agarose (Shelton Scientific, Shelton, Conn.) gel. Size separated nucleic acids were visualized following ethidium bromide (EB) staining and photographed using a Gel Doc 1000 video camera (Bio-Rad Laboratories, Hercules, Calif.). The PCR products were gel purified using Wizard PCR Preps (Promega, Madison, Wis.), and were directly sequenced using automated DNA Sequencing System Model 373A (Applied Biosysterns DNA Sequencer, Foster City, Calif.) following manufacturer's protocols for fluorescence-based DNA sequencing with Taq polymerase.

Partial sequences were compiled and aligned with somatic L-VDCC sequences (FIGS. 1 and 2A) with the MacVector 5.0 Program (Kodak, New Haven, Conn.). Secondary structure predictions were determined using PC/GENE Release 6.8, Oxford Molecular Group, Beaverton, Oreg.).

Statistical Analyses.

Data was analyzed using two-sample or paired t-test and ANOVA models.

Results

Four individual sperm RNA templates yielded a single PCR product of expected size (532 bp) with this specific pnrmer pair and all contained exon 8A, not seen in cardiac muscle. Use of each of the other four sperm RNA populations as template resulted in a unique pattern of expected and smaller size amplified products, with two of them exhibiting 2 additional products and the remaining having a single additional product. Two samples yielded a PCR product that was deleted in exon 8 completely, while others showed the presence of an alternative splice at exon 7 (encoding the extracellular loop between 155 and 156) that has not been previously described. The testis RNA template yielded all of the smaller size divergent products and confirmed prior findings on expression of both exons 8 and 8A.

L-VDCC and Sites of Exogenous Metal Ion Entry Co-localize on the Humoan Sperm Head.

To examine the involvement of sperm L-VDCC in transport of metal ions other than $Ca^{2+}$, motile sperm populations from four fertile donors were divided into aliquots and assessed for metal ion entry by autometallograpdy and for expression of the L-VDCC α1C subunit by indirect immunocytochemistry.

Figure 3B:
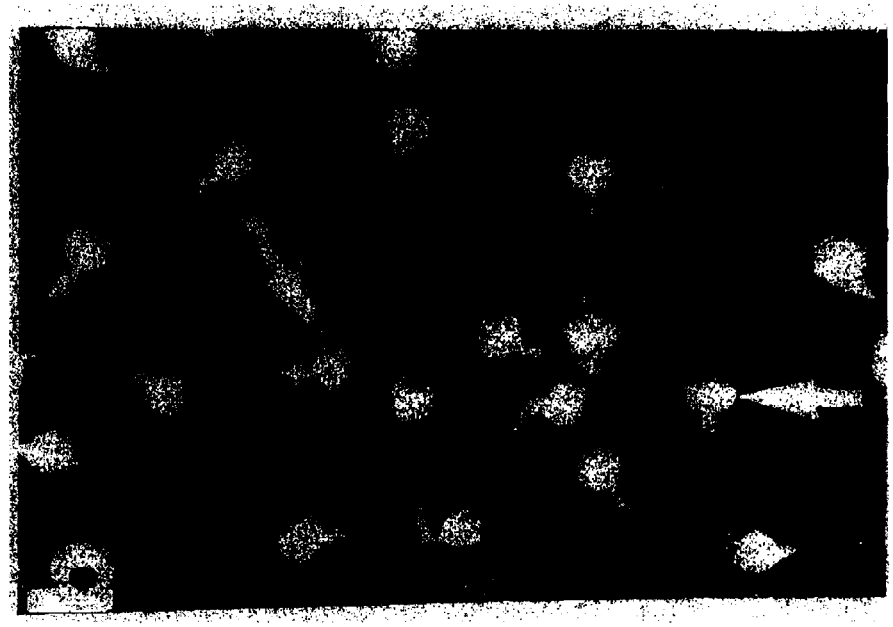
FIG. 3B is an epifluorescence image of a human sperm sample.
Figure 3A:
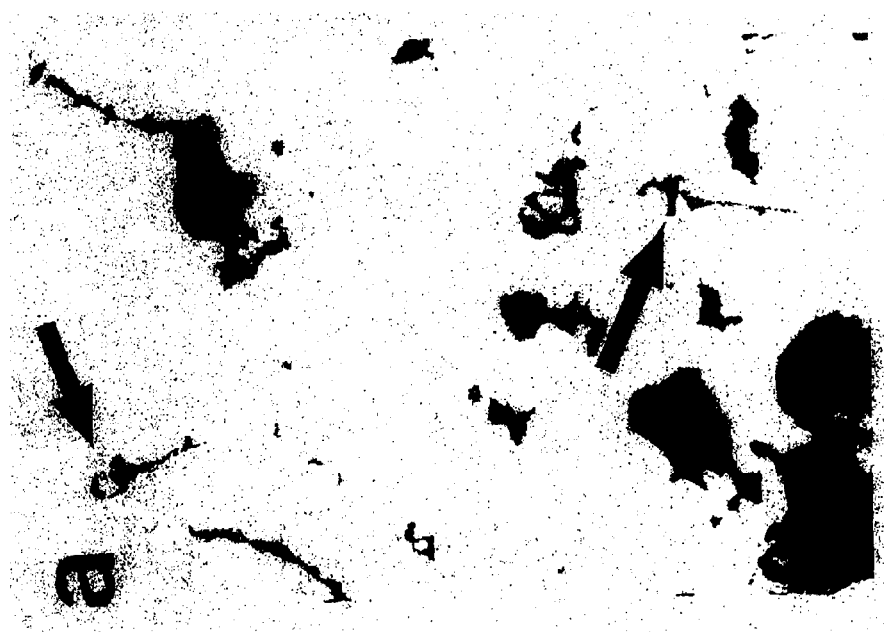
FIG. 3A is a phase-contrast image of a human sperm sample.

In addition to accumulation on the sperm tail, BSDs attributable to exogenous $Zn^{2+}$ entry were observed to concentrate in the equatorial and post-acrosome regions of the human sperm head (FIG. 3A). After overnight incubation in $Zn^{2+}$ supplemented media, 81.4±6.7% of all sperm displayed BSDs after physical devel opment. Control aliquots [1] not exposed to $Zn^{2+}$ but treated with sodium sulfide or [2] incubated with $Zn^{2+}$ but not treated with sodium sulfide exhibited only 0.4±1.1% of sperm with BSDs. Thus, $Zn^{2+}$ exposure was associated with a significant increase in sperm displaying BSDs (P<0.0001). The $Zn^{2+}$-induced BSDs were dissolved by exposure to 0.1 N HCl/1% KCN (7.8±5.2% of sperm having BSDs after treatment; P<0.04) but not by 1% $H_2O_2$ (87.0±7.4% of sperm with BSDs; P=0.3, N.S.).

Figure 4B:
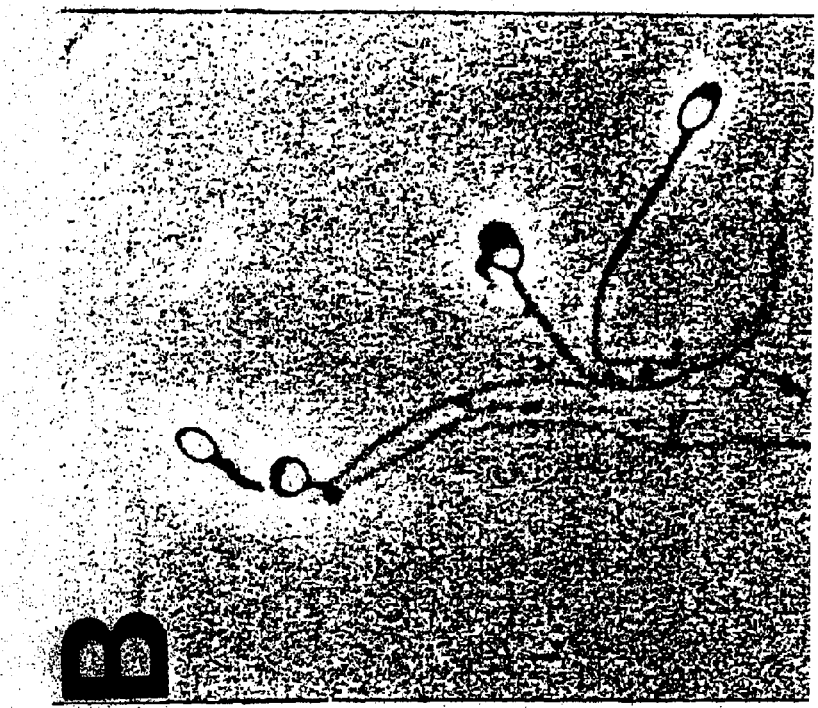
FIG. 4B is a phase-contrast image of a human sperm sample that is not exposed to $Cd^{2+}$.
Figure 4A:
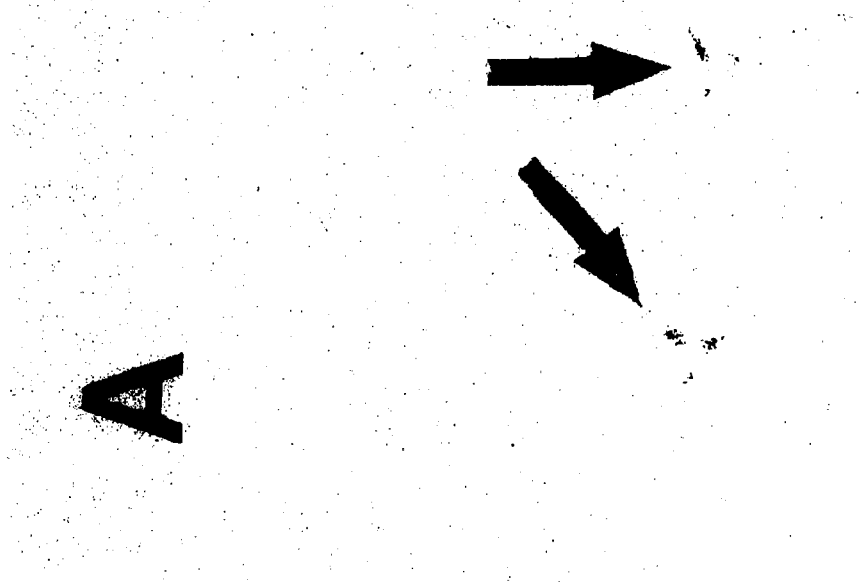
FIG. 4A is a phase-contrast image of a human sperm sample exposed to cadmium ($Cd^{2+}$)

FIGS. 4A and 4B relate to the exposure of human sperm to $Cd^{2+}$. Specimens were viewed and photographed as described for FIGS. 3A and 3B. Typical results are shown in FIGS. 4A and 4B from a specimen from one fertile donor. Sperm-associated $Cd^{2+}$ was detected by autometallography after overnight exposure to metal ions as described below. The arrow in FIG. 4A highlights BSDs in the equatorial and post-acrosome regions of the human sperm head. Note that the human spermn heads in FIG. 4A are significantly enlarged compared to those in FIG. 4B. As shown in FIG. 4B, no BSDs are detected in a control aliquot not exposed to $Cd^{2+}$. This aliquot was treated with sodium sulfide prior to physical development.

BSDs attributable to $Cd^{2+}$ exposure were limited to the equatorial and post-acrosome regions of the human sperm head (FIG. 4A), with 97.4±1.2% of sperm being scored as positive for BSDs. In contrast, only 3.2±1.3% of sperm in control aliquots not exposed to $Cd^{2+}$ exhibited BSDs. As for $Zn^{2+}$, $Cd^{2+}$ exposure was associated with a significant increase in sperm displaying BSDs (P<0.0001). These BSDs were dissolved by $H_2O_2$ (0.9±0.8% sperm with BSDs after treatment; P<0.0001) but not by HCL+KCN (96.1±0.5% BSDs-positive sperm; P=0.8, N.S.). It is important to note that sperm head shape was markedly changed after $Cd^{2+}$ exposure (i.e. from oval to amorphous; compare sperm head shape in FIG. 4A with that of the non-exposed control aliquot in FIG. 4B) but not after $Zn^{2+}$ exposure.

FIGS. 3A and 3B relate to co-localization of exogenous $Zn^{2+}$ and L-VDCC α1C antigenic epitopes in human sperm. All specimens were viewed at 600× magnification with an Olympus BX50 microscope (Olympus Corp., Lake Success, N.Y., USA). Where required for documentation, specimens were photographed using phase-contrast (for autometallography) and UV-epifluorescence (for indirect immunocytochemistry) illumination. Automatic exposure was employed for phase-contrast images (e.g., FIG. 3A) and manual exposure of 50 seconds was used for in epifluorescence images (e.g., FIG. 3B). All photographs were developed for the same length of time at 68° C. and printed with identical exposure times. Typical results are shown in FIGS. 3A and 3B from one fertile donor.

Sperm-associated $Zn^{2+}$ was detected by autometallography after overnight exposure to metal ions as described above. The arrows in FIG. 3A highlight BSDs in the equatorial and post-acrosome regions of the human sperm head.

To identify antigenic epitopes of L-VDCC on human sperm by indirect immunocytochemistry, mouse monoclonal antibody IIF7 served as primary antibody. This antibody specifically precipitates a 170 kDa protein from rabbit skeletal muscle triads, identified as the α1C subunit and dihydropyridine receptor of the rabbit skeletal muscle L-VDCC. Monoclonal antibody IIF7 specifically labels the equatorial and post-acromose regions of the human sperm head, indicated by arrows in FIG. 3B.

Antigenic epitopes of the L-VDCC α1C subunit were also found in the equatorial and post-acrosome regions (FIG. 3B). This labeling pattern differs significantly from that for anti-actin antibodies. Used as a control, Anti-actin antibodies bind over the anterior head of acrosome-intact sperm, but are limited to the equatorial segment of acrosome-reacted sperm (not shown). A total of 85.9±5.7% of all sperm bound the antibody directed against the L-VDCC dihydropyridine receptor. This value was indistinguishable from that for sperm exhibiting $Zn^{2+}$ or $Cd^{2+}$ entry (P=0.9, N.S.).

These data provide evidence that $Cd^{2+}$ and $Zn^{2+}$ enter the human sperm head at sites identified as L-VDCC, both by co-localization and by sperm head shape changes after $Cd^{2+}$ exposure. The latter implies that the exogenous $Cd^{2+}$ is interacting with actin filaments.

Cloning of the L-VDCC α1C Subunit Expressed in Human, Testis

The α1C subunit of the human testis L-VDCC is transcribed from a gene composed of >50 exons, with multiple isoforms produced as in somatic tissue as a result of alternative splicing (Table 1). These splices occur at the amino terminus and in transmembrane segments IS6, IIIS2 and IVS3. In somatic tissues, α1C subunits in human fibroblasts and heart differ at the amino terminus and in transmembrane segments IS6, III2 and IVS3 as a result of alternate exon usage, and contribute to the different gating properties of these channels. Although only the amino terminus used in fibroblasts is found in human testis, expression of both fibroblast and cardiac exons encoding transmembrane segments IS6, IIIS2 and IVS3 are observed (Table 1), helping to explain the unique electrophysiological properties of $Ca^{2+}$ currents in sperm. Similar regions of alternative splicing have been identified in L-VDCC α1C subunit transcripts expressed in rat testis.

Each cDNA clone used to construct the testis-specific L-VDCC α1C sequence encoded only one alternative splice site. Twelve different individual splicing variants were ultimately identified using testis rNRNA pooled from 20 men (Table 1). Prelinminary studies employing the HUCH 3F2/HUCH 6R2 (SEQ ID NO: 3/SEQ ID NO: 4) primer pair (which span exons 20–35) to determine which splicing events occur together in individual mRNA transcripts in pooled human testis RNA preparations unexpectedly revealed that some transcripts had deletions in exon 33 (which encodes the hinge between transmembrane segments IVS3 and IVS4) and/or exon 34 (transmembrane segment IVS4, the voltage-sensor).

Identification of Structure/function Relationships.

The fumctional significance of alternative splicing was examined using RNA templates prepared from motile sperm populations from ejaculated sperm from 9 different donors and the HUCH 3F2/HUCH 6R2 (SEQ ID NO: 3/SEQ ID NO: 4) primer pair.

Each template yielded a single PCR product, either an expected 1650 bp product containing the consensus testis (fibroblast)-specific exons 22 (transmembrane segment IIIS2) and 31 (transmembrane segment IVS3) or a deleted product missing exons 33 and 34 but still containing testis (fibroblast)specific exons 22 and 31. Aliquots of the sperm samples analyzed for α1C transcript expression were examined for the ability to undergo an acrosome reaction induced by model zona ligands containing mannose. This assay can be used to predict the outcome of in vitro fertilization.

Sperm with templates directing the synthesis of the full-length consensus testis-specific (α1C fragment (e.g., HS#6, FIGS. 2A and 2B) exhibited the expected 50% increase in agonist-stimulated acrosome loss following mannose treatment (e.g., see 18).

In contrast, sperm carrying a deleted α1C transcript (i.e., HS#1, FIGS. 2A and 2B) acrosome loss in agonist treated and control aliquots was low and indistinguishable.

These preliminary studies suggest that structure/function relationships exist and may contribute to inter-male differences in the ability to respond to physiological agonists of the acrosome reaction.

L-VDCC and Susceptibility to $Cd^{2+}$.

Although the relative frequency of usage of fibroblast-specific exons in human testis is greater than cardiac (Table 1), the alternate splicing seen in the L-VDCC α1C isoform predominantly inserts a transrnembrane segment IS6 characteristic of cardiac tissue and 9 residues preceding 156 that form part of the pore lining. Single amino acid substitutions in the region immediately preceding transmembrane segment 156 have been identified as contributing to $Cd^{2+}$-sensitivity or resistance of voltage-dependent ion channels. The relevant amino acids are encoded by exon 7. These include tyrosine and glutamic acid residues near the external mouth of the ion-conducting pore. Note that the cysteine residue at position 374 in $Na^+$ channels, which contributes to $Cd^{2+}$-resistance, is not present in related L-VDCC.

FIG. 1A is a deduced consensus amino acid sequence of testis specific L-VDCC α1C subunit. Table 1 of FIG. 1B is a catalog of individual splicing variants of the human testis α1C subunit. The consensus sequence of the L-VDCC α1C subunit expressed in human testis was compiled from 8 initial overlapping ≦1 KB. Ultimately, 120 such clones from human testis templates were analyzed. The deduced amino acid sequences of these cDNA clones were aligned with that of the human fibroblast L-VDCC α1C subunit (CACNL1A1, EMBL/GenBank Accession Nos. from Z26256 to Z26308) or with that of human heart (Accession No. L29529) and was found to be more similar to the fibroblast than the cardiac form.

It was determined whether use of exon 8 or exon 8A could affect metal ion sensitivity. The cardiac 156 sequence (exon 8) differs from fibroblast IS6 (exon 8A) at 4 of 25 residues (see FIG. 1A). Three of these replacements are conservative: isoleucine (I) to leucine (L), I to valine (V), and threonine (T) to serine (S). The fourth, I to phenylalanine (F), substitutes an aromatic hydrophobic residue for aliphatic hydrophobic residue. All three algorithms for predicting membrane-spanning structures that are available as PC/GENE programs (RAOARGOS; SOAP; HELIXMEM) agree that these changes should have little effect on the stability or length of the transmembrane IS6 helix.

In contrast, the replacements between the splice junction and the start of transmembrane segment IS6 in exon 8 (FIG. 6B) are consistent with functionally significant alterations in channel properties. The change in three adjacent residues (arginine [R] to tyrosine [Y], aspartic acid [D] to glutamic acid [E] and tryptophan [W] to leucine [L]) remove a sequence of high flexibility (FLEXPRO) that has a high probability of being associated with a β-turn (BETATURN). The R to Y change also replaces a positive charge on the side-chain with an aromatic hydroxyl that is potentially capable of complexing a metal ion. The D to E change moves a functional group with unshared pairs of electrons further from the peptide backbone by increasing side-chain length by $CH_2$. Three other replacements just upstream of the triplet have similar effects; an asparagine (N) to glutamine (Q) that moves unpaired electrons firther from the peptide backbone, and two V to methionine (M) that introduce sulfurs with unshared pairs of electrons. The overall effect of these changes upstream of transmembrane segment IS6 is to create a local structure that could have an increased binding affinity for metal ions such as $Cd^{2+}$.

Development of an Assay to Distinguish Between Exon 8 and 8A.

Figure 5A:
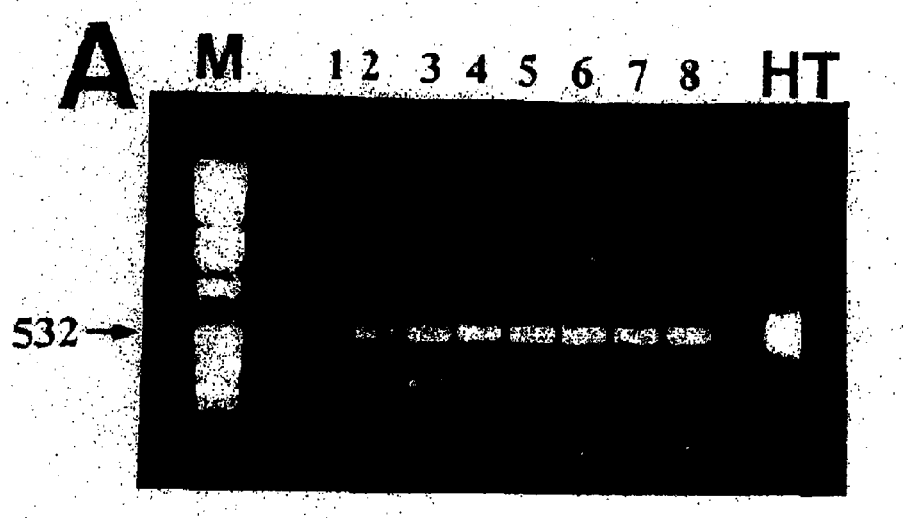
FIG. 5A illustrates an electrophoresis analysis of the PCR product of 7 human sperm templates.
Figure 5B:
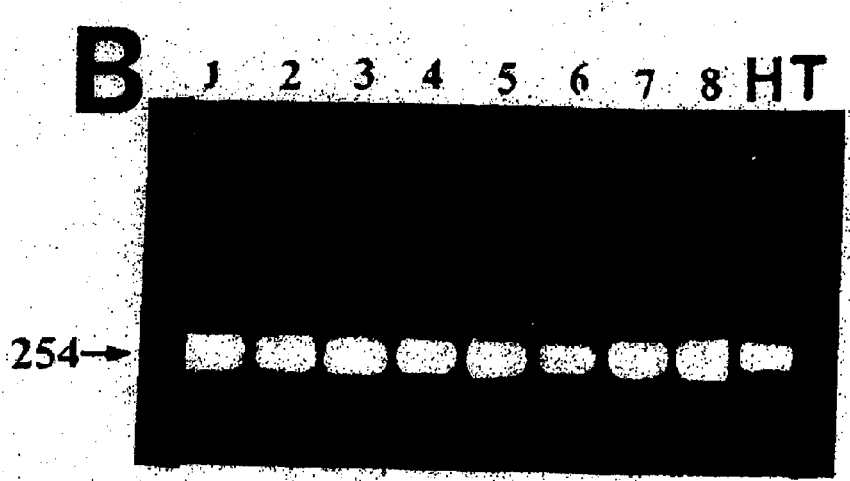
FIG. 5B illustrates an electrophoresis analysis of the PCR product of 8 human sperm templates.

FIGS. 5A and 5B relate to the initial analysis of PCR products obtained using the HUCH 2F/HUCH 1611R (SEQ ID NO: 1/SEQ ID NO: 2) and HG 690F/HG 984R (SEQ ID NO: 5/SEQ ID NO: 6) primer pairs. PCR products were size separated on 1.2% agarose gel in the presence of molecular weight standard (M represents 1 Kb ladder).

As shown in FIG. 5A, human sperm templates HS#2 to #8 and human testis (HT) all yielded a PCR product of expected size (532 bp; arrow) when amplified using the HUCH 2F/HUCH 1611R (SEQ ID NO: 1/SEQ ID NO: 2) primer pair. PCR products of lower molecular weight were also noted in reactions using HS#3, HS#7, HS#8 and HT templates. The absence of detectable PCR products in the lane from HS#1 is an artifact of the particular gel run. Re-analysis revealed a single product of expected size (see FIG. 9).

As shown in FIG. 5B, all 8 independent sperm RNA templates (HS#1–8) and human testis template yielded a single product of expected size (254 bp; arrow) when amplified using the hGAPDH-specific primer pair.

To develop a reliable assay for identification of expression of exon 7 and exon 8 versus SA in testis/sperm L-VDCC α1C transcripts, PCR primers were designed to sequences from exon 6 and exon 9 (FIGS. 1 and 2A). Both RNA preparations from 8 individual semen donors and from pooled human testis served as templates in these studies (FIG. 5A). To confirm that biologically active RNA (e.g., intact) was present in all templates tested, a second PCR reaction was performed using primers to a ubiquitously expressed "housekeeping" gene, hGAPDH. All templates produced a robust PCR product of the expected size, 254 bp, and sequence (FIG. 5B).

When a small aliquot of the PCR products resulting from template amplification with the HUCH 2F/HUCH 1611R (SEQ ID NO: 1/SEQ ID NO: 2) primer pair were analyzed under standard conditions by electrophoresis through a 1.2% agarose gel containing ethidium bromide, it was clear that all sperm templates and the pooled human testis template directed the synthesis of a 532 bp product (FIG. 5A; also FIG. 9), which corresponds to the expected size for the region of the α1C subunit to be amplified using primers HUCH 2F/HUCH 1611R (SEQ ID NO: 1/SEQ ID NO: 2) (nucleotides 1079–1611; see FIG. 1A). Further, in the gel lanes containing PCR products derived from human sperm templates HS#3, HS#7, and HS#8 and pooled human testis template, additional ethidium stained bands were detected which migrated more rapidly than the 532 bp product (FIG. 5A).

Figure 6A:
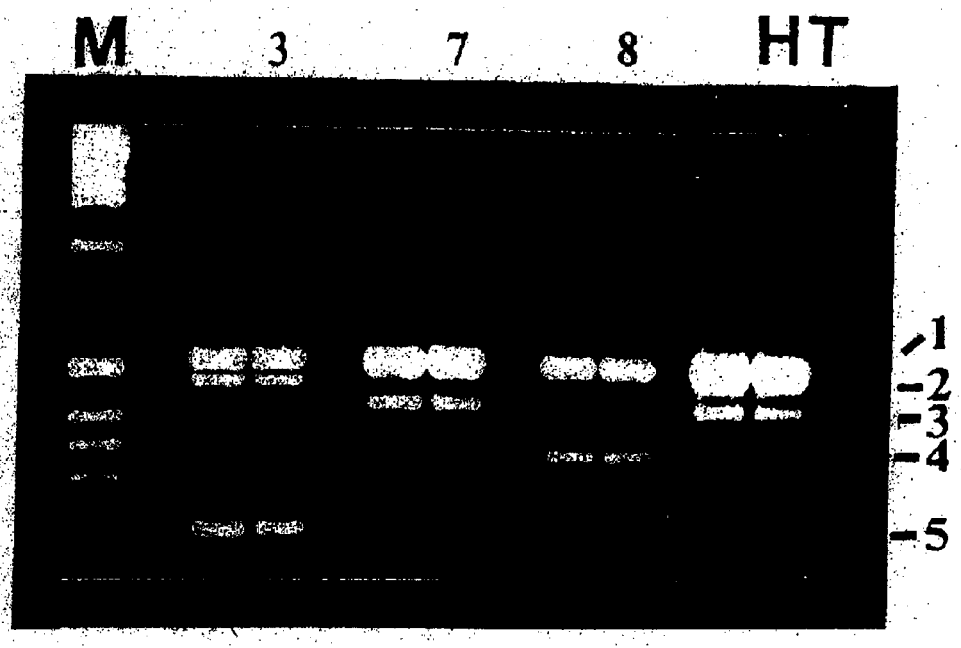
FIG. 6A illustrates an electrophoresis analysis of the PCR product of 3 human sperm templates.
Figure 6B:
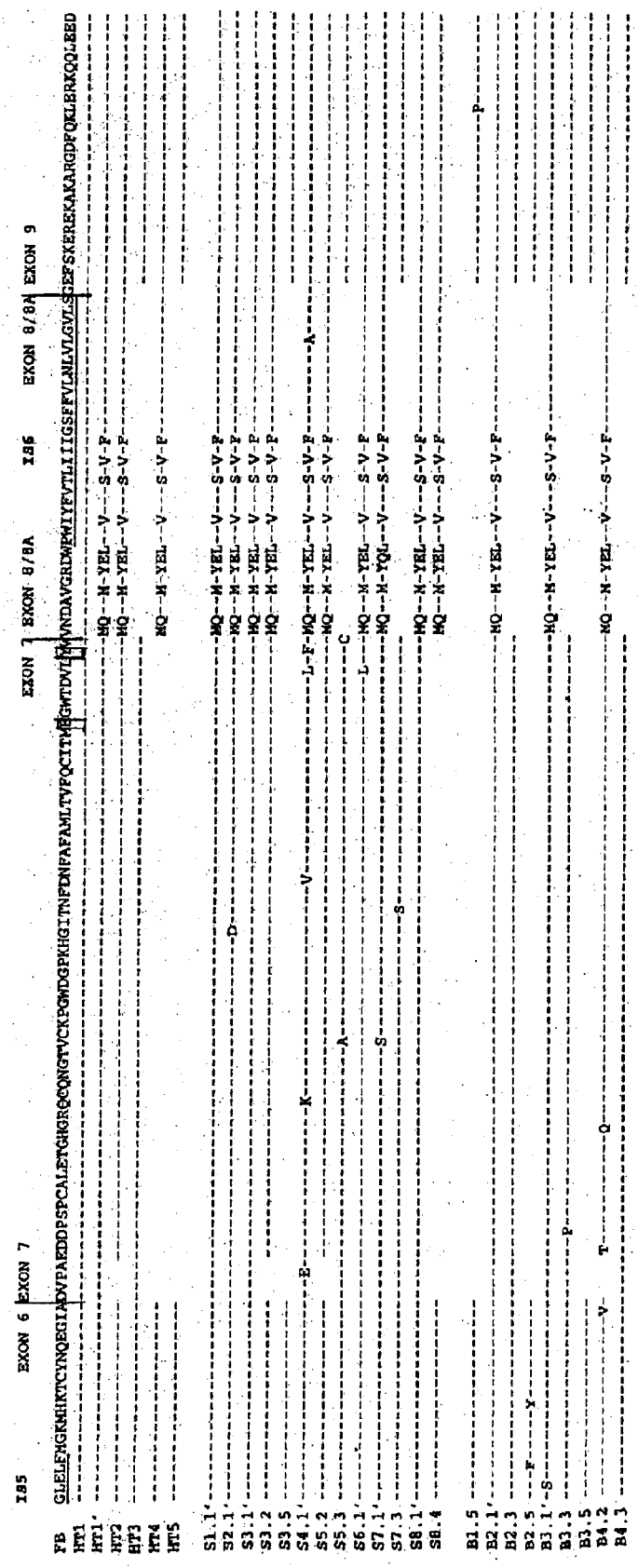
FIG. 6B illustrates the results of an automated sequence analysis of PCR products from a human testis template.

FIGS. 6A and 6B illustrate multiple PCR products obtained using the HUCH 2F/HUCH 1611R (SEQ ID NO:

1/SEQ ID NO: 2) primer pair. As shown in FIG. 6A, PCR products form human sperm templates HS#3, #7 and #8 and from pooled human testis template (HT) (see FIG. 5A) were reanalyzed by electrophoresis through a 2% low melting point agarose gel. Five PCR products could be distinguished on the basis of size relative to the molecular weight standard (M; 1 kB ladder): [1] a 532 bp fragment of expected size, [2] 520 bp, [3] 429 bp, [4] 335 bp, and [5] 232 bp. All 5 PCR products were obtained with human testis RNA template. Various combinations of these PCR products were obtained with templates from different sperm donors.

As shown in FIG. 6B, PCR products from human testis template were subjected to automated sequence analysis. PCR fragment 1 (532 bp) encoded a complete sequence, utilizing either exon (cardiac) or exon 8A (fibroblast). These sequences are indistinguishable on the basis of size or gel migration. PCR fragment 2 (520 bp) encoded a fragment utilizing a cryptic splice site at the beginning of exon 7, and resulting in a deletion of 12 bp. PCR fragment 3 (429 bp) was deleted in exon 8 (103 bp). PCR fragment 4 (335 bp) resulted from a deletion in exon 7 (197 bp). PCR fragment 5 (232 bp) was produced from a transcript deleted in both exons 7 and 8.

The deduced amino acid sequences of the individual PCR fragments were aligned with that of the analogous region of the fibroblast-specific sequence (FB). The positions of transmembrane segments IS5 and IS6 are delineated by underlining in FIG. 6B. Exon/exon boundaries are indicated by a vertical line. The two armino acids indicated in boxes represent those previously implicated in regulation of $Cd^{2+}$ sensitivity or resistance of somatic voltage-gated ion channels.

DNA sequence analysis confirmed that the PCR product obtained with different human sperm RNA (HS#1–#8= "S1–8") and human testis biopsy (TB#1–#4="B1–4; see FIG. 9) templates were similar to those in normal pooled testis.

To optimize visualization and separation of PCR products with slight molecular weight differences, potentially reflecting splice variants, the remainder of the PCR reactions was electrophoresced through a 2% low melting point agarose (Scientific Imaging Systems, Eastman Kodak Co, Rochester, N.Y.) gel (FIG. 6A) and the various PCR products were excised from the gel in preparation for DNA sequence analysis.

Ultimately, 5 PCR products of differing sequence were identified in reactions with a human testis RNA template (FIG. 6B). Product #1 was 532 bp in length and encoded two complete sequences for the region in question, nucleotides 1079–1611, i.e., either containing exon 8 (HT1'; cardiac, predicted to be more $Cd^{2+}$-sensitive) or exon 8A (HT1'; fibroblast, predicted to be less $Cd^{2+}$-sensitive). Product #2 (HT2), 520 bp in length, encoded a fragment that utilized a cryptic splice site at the beginning of exon 7 that resulted in a deletion of 12 bp. Product #3 (HT3) was deleted in exon 8 (103 bp) and was only 429 bp long. Product #4 (HT4), 335 bp, contained a 197 bp deletion of exon 7. Product #5 (HT5), 232 bp, was produced from a transcript deleted in both exons 7 and 8.

Various combinations of these PCR products were obtained with templates from different sperm donors (FIG. 6B). This is in direct contrast to the single PCR product obtained from individual sperm templates using the HUCH 3F2/HUCH 6R2 (SEQ ID NO: 3/SEQ ID NO: 4) primer pair (see above). In addition, a large number of single amino acid changes were identified (FIG. 6B). More single base substitutions were identified than those that affected the deduced amino acid sequence of this region of the α1C subunit.

L-VDCC α1C Isoforms in Infertile Men with Varicocele.

Figure 7A:
FIG. 7A illustrates an indirect immunofluorescence (anti-actin) image of seminiferous tubules from a formalin-fixed human testis biopsy.
Figure 7B:
FIG. 7B illustrates an indirect immunofluorescence (anti-actin) image of seminiferous tubules from a formadin-fixed human testis biopsy.
Figure 7C:
FIG. 7C illustrates an indirect immunofluorescence (anti-actin) image of seminiferous tubules from a formalin-fixed human testis biopsy.

FIGS. 7A, 7B and 7C are a series of indirect immunofluorescence (anti-actin) images of seminiferous tubules form formalin-fixed human testis biopsies. Testis sections were reacted sequentially with primary antibody (rabbit anti-actin polyclonal sera) and human serun protein-preabsorbed, fluorescein isothiocyanate (FITC)-conjugated sheep anti-rabbit IgG for 1 hour each at room temperature. Control reactions employed pre-immune rabbit sera or secondary antibody alone. Slides were stored at 4° C. and scored within two weeks of staining. Stained testis sections were viewed at 600×. Identical fields were photographed on 35 mm/400 ASA TMAX film using UV-epifluorescence illumination with 50 second exposures. FIG. 7A is an image of a biopsy from a patient with obstructive azoospermia (0.3 ng $Cd^{2+}$/mg dry weight). FIG. 7B is an image of a biopsy from an infertile subject with varicocele and hypospermatogenesis (0.5 ng $Cd^{2+}$/mg dry weight). FIG. 7C is an image of a biopsy from an infertile subject with varicocele and hypospennatogenesis (1.1 ng $Cd^{2+}$/mg dry weight). In FIGS. 7A, 7B, and 7C anti-actin staining decreases as $Cd^{2+}$ levels increase. Further description of the images found in FIGS. 7A, 7B and 7C may be found in Benoff, S., Gilbert, B. R., Varicocele and male infertility: Part I Preface, Human Reroduction Update, 7:47–54, 2001, the entire contents and disclosure of which is hereby incorporated by reference.

Figure 8A:
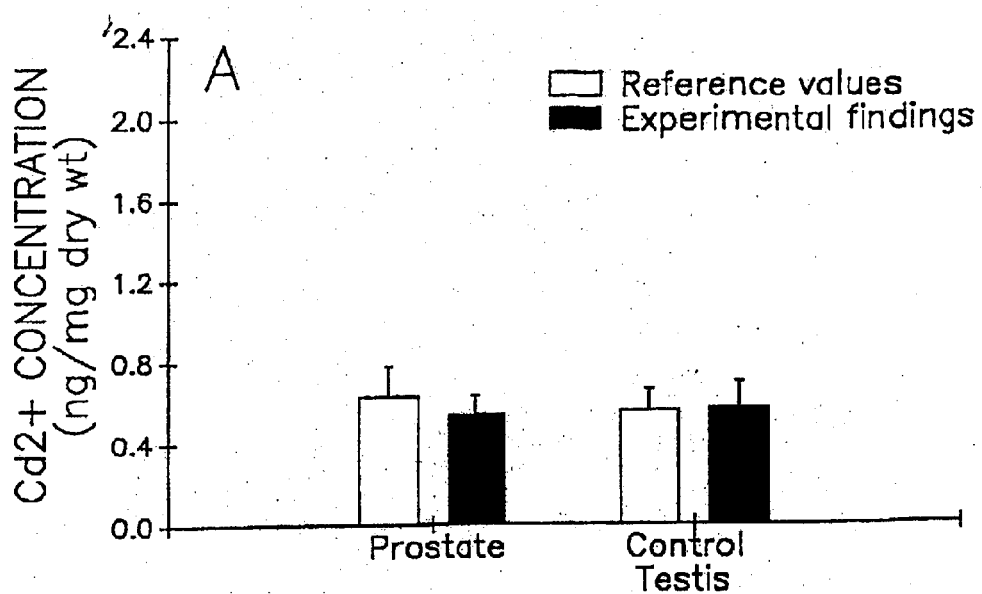
FIG. 8A is a graph illustrating that apoptosis increases with increasing testicular $Cd^{2+}$ levels.
Figure 8B:
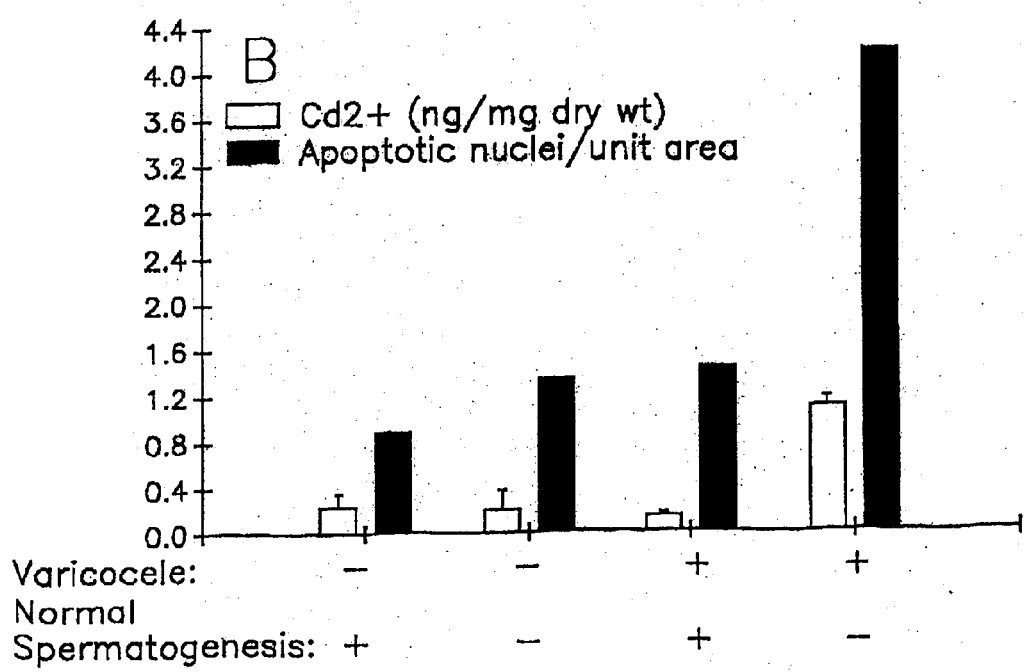
FIG. 8B is a graph illustrating that apoptosis increases with increasing testicular $Cd^{2+}$ levels.

FIGS. 8A and 8B illustrate the results of a TUNEL assay of human testicular biopsies that show apoptosis increases with increasing testicular $Cd^{2+}$ levels. To validate tissue $Cd^{2+}$ measurements by atomic absorption spectroscopy, values obtained for normal prostate and testis (from men with obstructive azoospermia) were compared with values reported in the literature, as shown in FIG. 8A. The values obtained were indistinguishable from those reported by other laboratories. $Cd^{2+}$ levels and apoptosis were assessed in testicular biopsies from men with obstructive azoospermia (n=2; "Varicocele–, Normal Spennatogenesis+"), Sertoli cell only syndrome (n=2; "Varicocele+, Normal Spermatogenesis–"), varicocele with normal spermatogenesis (n=3; "Varicocele+, Normal Spermatogenesis–"). In the analysis of apoptosis, seminiferous tubules were measured with a micrometer eyepiece. The area was computed from the formula: $\pi r^2$. Apoptotic nuclei were scored per unit area of tubule. $Cd^{2+}$ levels and degree of apoptosis differed significantly among the three groups studies (respectively, P<0.02 and P<0.001).

Four testis biopsies (TB#1–#4) were chosen for analysis in this preliminary study from among 9 that had previously been characterized with regard to actin content (FIGS. 7A, 7B and 7C), $Cd^{2+}$ concentration (FIGS. 8A and 8B) and level of apoptosis (FIG. 8). TB#1 was from a subject with Sertoli cell only syndrome, TB#2 and TB#3 were from infertile men with varicocele with normal spermatogenesis, and TB#4 was from an infertile man with varicocele with hypospermatogenesis. RNA isolated from these testis biopsies was amplified using the HUCH 2F/HUCH 1611R (SEQ 1) NO: 1/SEQ ID NO: 2) primer pair in order to examine expression of the region of the α1C subunit potentially regulating response to $Cd^{2+}$ (FIGS. 6B and 9).

Figure 9:
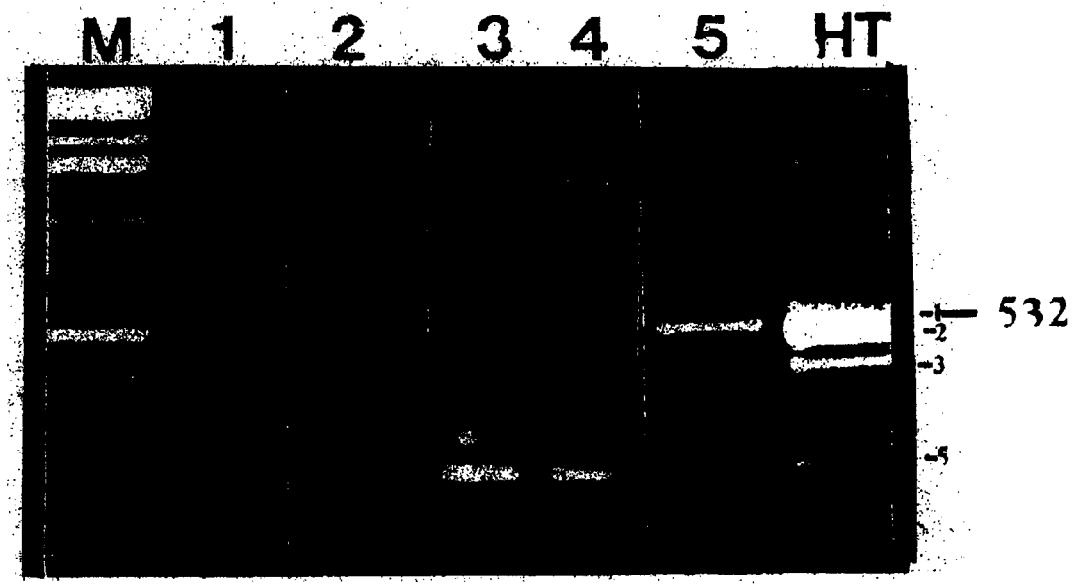
FIG. 9 illustrates an electrophoresis analysis of RNA obtained from individual human testis biopsies using the HUCH 2F/HUCH 1611R (SEQ ID NO: 1/SEQ ID NO: 2) primer pair.

FIG. 9 relates to the amplification of RNA obtained from individual human testis biopsies using the HUCH 2F/HUCH 1611R (SEQ ID NO: 1/SEQ ID NO: 2) primer pair. PCR products were size separated by electrophoresis through a 2% low melting point agarose gel containing ethidium bromide in the presence of a molecular weight marker (M; 1 Kb ladder). The PCR products generated form [1] TB#4, [2] TB#1, [3] TB#3, [4] TB#2 and [5] human sperm HT#1

RNA templates were compared with those obtained using normal pooled testis RNA as template. Four of the five PCR products in normal testis were also detected in various combinations in the individual testis biopsies. Product 1 is 532 bp, product 2 is 520 bp, product 3 is 429 bp and product 5 is 232 bp.

TB#1 expressed only a single α1C transcript of 232 bp (FIG. 9). Three PCR products (532 bp, 429 bp, 232 bp) were obtained using either RNA from TB#2 or TB#3 as template. In contrast, DNA fragments of 520 bp and 429 bp were amplified from the TB#4 RNA template. DNA sequence analysis (FIG. 6B) indicated that when present, only exon 8 (cardiac) was used in these transcripts. Further, this analysis confirmed that each 532 bp product encoded the expected full-length sequence, and expressed the exon 8 (cardiac), that each 520 bp product used the cryptic splice site in exon 7, that each 429 bp product had a deletion of exon 8 and that exons 7 and 8 were deleted from each 232 bp product. Single amino acid substitutions were also observed, especially in the PCR products generated from TB#4. Thus, normal α1C transcripts were not detected in specimens defined as having a hypospermatogenic state.

Potential Consequences of the Observed Variability in Exons 6–9 of the L-VDCC α1C Transcript.

Figure 2B:
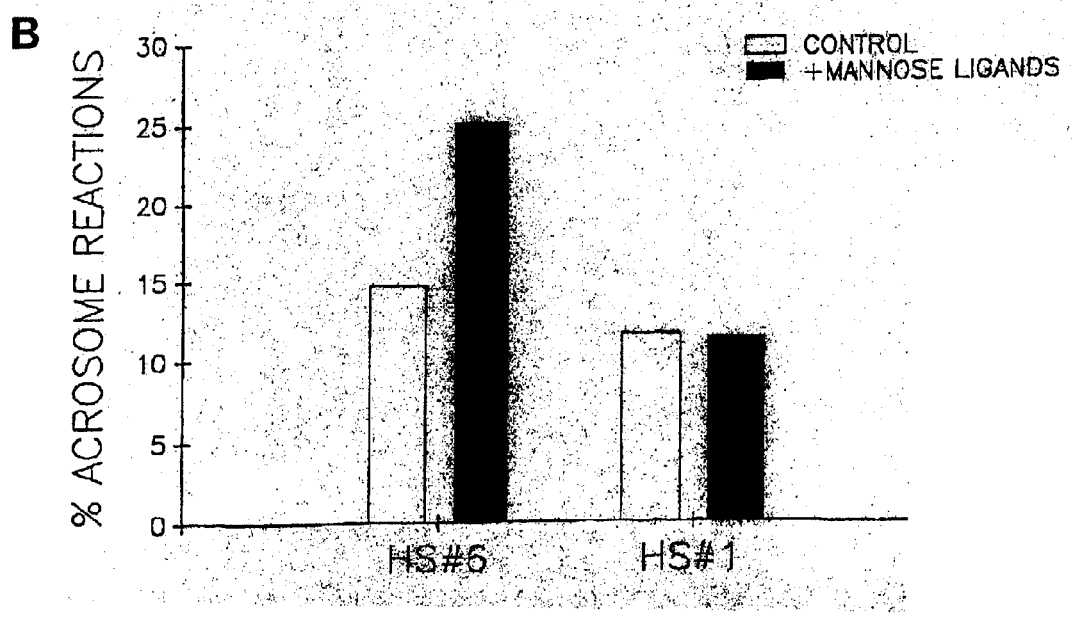
FIG. 2B is a graph comparing mannose-stimulated acrosome loss from two different sperm specimens.

FIGS. 2A and 2B relate to the identification of structure/function relationship for the human sperm L-VDCC α1C subunit. The α1 subunits of L-VDCC and related voltage-gated $Na^+$ and $K^+$ channels are derived from a common ancestor. The basic α1 subunit is composed of four repeated domains (I–IV), each containing six putative transmembrane segments (S1–S6). Transmembrane segment S4 is the voltage sensor. The regions between transmembrane segments S5 and S6 (SS1–SS2) line the ion conducting pore and contain binding sites for metal ions. Multiple L-VDCC α1 isoforms (e.g., (α1A, α1B, α1C, α1D, α1E) are generated by transcription of different genes and by alternate splicing of the primary transcript from each gene. The α1C subunit forms the pore of the L-VDCC expressed in mammalian testis and sperm and is alternatively spliced at the amino terminus and transmembrane segments IS6, IIIS2 and IVS3 (see Table 1). This subunit contains the binding sites for a variety of pharmacological agents, including dihydropyridines which are prescribed for hypertension control and which may produce a reversible infertile state. The dihydropyridines bind within the alternatively spliced transmembrane regions IS6, IIIS2 and IVS3.

Transcripts encoding the L-VDCC α1C subunit may be amplified from RNA templates isolated from ejaculated motile human sperm populations. Preliminary studies have examined which splicing events regulating expression of transmembrane segments IS2 and IVS3 occur together (exons 20–35). RT-PCR simplified both products of expected size (i.e., HS#6) and shorter sequences (i.e., HS#1).

Mannose-stimulated acrosome loss was compared in sperm from specimen HS#6 having the consensus testis-specific L-VDCC α1C sequence with sperm from specimen HS#1. After mannose treatment, as described below, sperm were scored as [1] acrosome-intact if the anterior and equatorial regions of the head were uniformly RITC-PSA labeled, or as [2] acrosome-reacted if only the equatorial segment was labeled or if the sperm heads were completely RITC-PSA negative. At least 300 sperm in a minimum of 20 microscopic fields were scored for acrosomal status.

A four amino acid deletion (DVPA) at the start of exon 7 is a common feature of the non-consensus testis (fibroblast) (HT1-like) or cardiac (HT1-like) DNA fragments amplified using the HUCH 2F/HUCH 1611R (SEQ ID NO: 1/SEQ ID NO: 2) primer pair and templates from pooled normal human testis, individual testis biopsies or ejaculated motile human sperm. It was found in HT2, S3.2, S5.2 and B4.2 (FIG. 6B). This deletion does not appear to have a significant effect on local secondary structure. The explanation of any functional consequences of this deletion must be found in specific interactions involving these residues. Specific interactions involving both other amino acids and metal ions plausibly exist here, since the pore-lining structures SS1 and SS2 lie between transmembrane segments IS5 and IS6 (see FIGS. 2A and 2B). Aspartate (D), for example, if it lies in a region of extended structure, may be available to coordinate with metal ions despite its relatively short side-chain. Altering the local structure of the pore lining can potentially affect the ion transport properties of the pore. Thus, loss of D might contribute to $Cd^{2+}$-resistance.

PC/GENE analysis of deleting exons 7 and 8/8A provided no surprises. Both HELIXMIEM and SOAP predicted that deletion of exon 8/8A removed one membrane-spanning helix whose predicted location agreed well with the consensus position of transmembrane segment IS6. This deletion did not affect the stability or location of other predicted helices, nor did it predict that a new helix would be created as a result of this deletion. Deletion of exon 7 did not change the helices predicted by SOAP. HELIXMEM predicted a transmembrane multimeric helix in exon 7, possibly corresponding to SS1 and SS2. Deletion of exon 7 caused HELIXMEM to remove that helix, and make no other changes in its predictions.

Both conservative and non-conservative single amino acid substitutions are found in the IS5–IS6 region in many of these DNA fragments (FIG. 6B). Only S6.1' and S7.1' lack both a deletion and at least one non-conservative replacement. Therefore, only the non-conservative changes are addressed here.

Most of the non-conservative changes introduce or remove charged groups or terminal polar substituents in the pore lining structures SS1 and SS2. Modeling with PC/GENE indicated that, with the possible exception of B3.1' these substitutions did not significantly affect the local secondary structure. In B3.1', serine (S) replaced leucine (L) at the carboxy-terminal end of transmembrane segment IS5 and appeared to further stabilize that trans-membrane helix. In contrast, the non-conservative single amino acid substitutions may effect the ion transport properties of the pore through specific interactions with metal ions or by changing the pore radius allosterically.

Conclusions.

Prior studies have shown that, a series of amino acid substitutions occur within the region in and around IS6. The present invention shows that this region also shows significant diversity with respect to splice junction usage. In contrast to earlier observations, there appears to be more than one transcript present in individual sperm samples, consistent with the detection of multiple $Ca^{2+}$ currents in immature germ cells. The planned examination of L-VDCC α1 isoform expression in VAI by this protocol is likely to provide insight into the combination of genes and environment that influence this disease. (Support: NIH Grants No. ES 06100 and ES 10496 to S.B.)

The current studies were performed in preparation for a large prospective study of the genes and environmental influences producing varicocele-associated infertility. Further testing may be conducted on whether measurements of scrotal temperatures, determination of $Cd^{2+}$ concentrations in testis biopsies and expression of specific L-VDCC α1C isoforms may serve as biomarkers for the identification of the subgroup of men with varicocele-associated infertility who will favorably respond to varicocele surgery. A series of studies already suggest that biomarker measurements are useful in determining the treatment options available to a given infertile male with varicocele, e.g., repair versus IVF versus IVF1/ICSI. Specifically, in a retrospective analysis of 20 infertile men with varicocele, measurements of mannose receptor expression and mannose-stimulated acrosome loss before varicocele repair and seminal plasma $Cd^{2+}$ levels after varicocelectomy differentiated between those men able to initiate a pregnancy by coitus after surgery from those who did not.

Currently, indications for varicocele repair include: [1] at least two abnormal semen analyses, [2] two abnormal sperm penetration assays, [3] failed or reduced fertilization in in vitro fertilization (IVF), [4]>20% decrease in testicular volume, and [5] scrotal discomfort or disfigurement. However, co-existing pathology can decrease the success rate of treatment. Varicocele repair has not improved pregnancy rates when the varicocele was associated with: [1] azoospermia with elevated serum FSH levels, [2] obstructive azoospermia, [3] male accessory gland infection, and [4] immunological factors. In addition, there is a relatively high recurrence (20%) of varicocele after repair. Given the existence of alternative treatments to achieve conception, optimal treatment requires pre-selection of those patients for whom repair would be most beneficial.

The need for pre-selection is supported by a variety of studies. For example, men with larger varicocele appear to have greater post-repair improvement in semen parameters and pregnancy rates than men with small varicocele. In addition, the same semen abnormalities are observed in both fertile and infertile men with varicocele. There is no correlation between the improvement in semen parameters and testicular volume post-surgical varicocele repair. Most importantly, an improvement in semen quality is observed more frequently after repair than is the ability to initiate a pregnancy. In other words, some infertile men respond to varicocelectomy with a consequent return of fertility while others do not.

There is strong evidence that an environmental factor ($Cd^{2+}$) interacts with a host factor (varicocele) to produce an infertile state. Preliminary findings described herein suggest that endogenous gene expression (L-VDCC isoforms) also contribute to infertility, with varicocele.

The full-length transcript of the LVDCC α1C subunit expressed in normal human testis has been cloned and sequenced according to the present invention. It is transcribed from the same gene that encodes the fibroblast- and cardiac-specific isoforms. Multiple α1C transcripts are expressed in human testis as the result of alternative splicing at the 5' end (amino terminus) and in regions encoding transmembrane segments IS6, IIIS2 and IVS3. With regard to varicocele-associated infertility, efforts are focused on defining the role of variations in the amino acid sequence in and around transmembrane segment IS6. Domain I of the L-VDCC α1C subunit may be very useful in determining $Ca^{2+}$ channel activation kinetics and whether the subdomain of interest regulates voltage-dependent inactivation.

Some L-VDCC α1C transcripts in human testis and sperm are deleted in exons 7 (SS1–SS2=lining of ion-conducting pore) or 8 (SS2/IS6) or exons 7 and 8. In somatic cells, deletions in the L-VDCC α1C subunit have been associated with changes in the mechanism regulating channel opening, with increased expression, and with complete loss of function. Mutant/truncated α1C subunits (e.g., lacking IS1 through IS4) are still able to form a functional channel when co-expressed with auxiliary subunits in Xenopus oocytes. Therefore, there is some uncertainty as to how observed deletions affect channel function. Empirical observations, such as made for the effect of deletion of exons 33 and 34 on agonist-stimulated acrosome loss, may be required.

There is, however, a precedence for defective ion transport as the underlying cause of at least one form of human male infertility. From other studies, a body of evidence has been accrued indicating that ion channel isoform expression regulates resistance to the deleterious effects of another exogenous metal ion, $Pb^{2+}$. Therefore, it is striking that the present invention did not amplify a normal "consensus" α1C transcript from RNA from testis biopsies from hypospermatogenic states. These transcripts were both deleted and also exhibited non-conservative amino acid changes in the lining of the ion-conducting pore.

The amino acid sequences immediately preceding transmembrane segment IS6 regulate $Cd^{2+}$ sensitivity or resistance. Specifically, $Cd^{2+}$ competes with $Ca^{2+}$ for high-affinity binding sites near the external mouth of the ion-conducting pore. Rapid permeation of $Ca^{2+}$ through L-VDCC requires that at least two $Ca^{2+}$ be bound at these high-affinity sites. Thus, $Cd^{2+}$ binding at these sites occludes $Ca^{2+}$ entry into the L-VDCC ion-conducting pore. Membrane depolarization, required for L-VDCC opening, enhances $Cd^{2+}$ entry into cells. Therefore, the variability in this region reported herein may contribute to altered ion transport and "susceptibility" to environrmental/occupational exposure to transition and heavy metal ions.

Marmar emphasizes the clinical diversity of human varicocele (e.g., inter-male differences in scrotal temperatures, semen analysis and histology of testis biopsies) as compared to the relative uniformity of findings in experimental animal models. With this in mind, the present invention suggests other mechanisms to produce apoptosis and that an irreversible infertile state may be operational in addition to increased ill, intratesticular $Cd^{2+}$ levels/specific L-VDCC α1C isoforms expression. For example, Marnar suggests that androgen receptor defects may be a contributing factor.

In FIG. 10, there is outlined a model for the interaction of three pathways in the production of varicocele-associated apoptosis and oligozoosperrnia: [I] elevated scrotal temperature (heat stress), [II] increased intratesticular $Cd^{2+}$ concentrations, and [III] androgen deprivation. Further description of the model outlined in FIG. 10 may be found in Benoff, S., Gilbert, B. R., Varicocele and male infertility: Part I Preface, Human Reroduction Update, 7:47–54, 2001, the entire contents and disclosure of which is hereby incorporated by reference.

Pathway I involves heat stress. In this pathway, the cryptorchidism in man is associated with high scrotal temperature, impaired spermatogenesis and infertility. Clearly, human sperm motility may be adversely affected by high temperatures. Elevated temperatures are also known to be an external modifier of action polymerization. In animal models, intracellular actin is disrupted by a brief local heating of the scrotum. Thus, studies in animal models suggest that this heat-induced infertility is due, at least in part, to increased testicular germ cell apoptosis. In the cryptorchid rat, exposure of the testis to the higher abdominal temperature potentiates the toxic effects of $Cd^{2+}$ exposure.

Pathway II invokes mechanisms based on increased intratesticular $Cd^{2+}$ levels and is the pathway being dissected. In this pathway, the interstitial fluid in the testis is a filtrate from blood plasma, with capillary hydrostatic pressure and interstitial fluid pressure determining the volume of interstitial fluid. Varicocele causes an increase in testicular venous pressure and increasing fluid transport. Thus, the elevation in testicular $Cd^{2+}$ concentration observed in varicocele-associated infertility is likely to be derived from the increased transvascular fluid exchange that occurs with varicocele. This means that there is the potential for more of the $Cd^{2+}$ in serum to enter the testis. Such entry is likely to occur as animal studies have provided clear evidence that $Cd^{2+}$ exposure alters the permeability of the testicular vascular endothelium. As there is no active pump to remove this $Cd^{2+}$, testicular $Cd^{2+}$ exposures damage vascular endothelial cells, resulting in edema allowing greater access to testicular parenchyma. Data suggests that entry of $Cd^{2+}$ into the cells of the seminiferous epithelium may occur via L-VDCC, which are expressed in all cells with the seminiferous epithelium. $Cd^{2+}$ action in the testis is likely to be cell-specific and stage-specific. Sertoli cells have been reported to be differentially sensitive to $Cd^{2+}$. Intracellular Sertoli cells apparently regulate spermiation and movement of spermatocytes through the blood-testis barrier. A single low dose of $Cd^{2+}$ causes both disruption of Sertoli cell microfilaments and failure of spermiation, potentially contributing to oligozoospermia. By analogy with findings in somatic cells, $Cd^{2+}$-induced loss of cytoplasmic actin filaments should increase apoptosis and contribute to the production of oligozoospermia. Intracellular $Cd^{2+}$ should also directly stimulate the $Ca^{2+}$-dependent endonuclease that produces DNA fragmentation leading to apoptosis.

Pathway III is the result of androgen deprivation, which may result from endocrine dysfunction or from an androgen receptor defect.

The present invention proposes an interaction between $Cd^{2+}$ and androgen deprivation based on two sets of observations. First, varicoceles appear at puberty. Second, the susceptibility of the testis of animal models to $Cd^{2+}$-induced damage is thought to be androgen dependent, as newborn animal testis are resistant with the severity of $Cd^{2+}$-induced damage increasing with age. This interaction is eminently testable through the examination of human testis biopsies, such as used in this study.

Testis biopsies are normally used for examination of testicular histology and sperm retrieval for assisted reproduction. One group has also used testis biopsies pre- and post-repair to demonstrate the efficacy of varicocele surgery. Preliminary findings suggest that spermatogenesis as assessed in testis biopsies may be predictive of the outcome of varicocele repair. The technique of aspiration biopsy was used in this study. Prior studies have shown that there is minimal trauma to the patient and the testicular tissue so obtained is well preserved within the angiocath so that the histology has demonstrated no distortion when compared to open biopsy material from the same patient. The current findings suggest that aspiration biopsy of the testis could become part of the infertility workup of the future, which will include immunohistochemical and molecular studies.

Example 3

L-VDDC α1C transcript structure in testis biopsies from 39 men was examined. Three biopsies were from men with obstructive azoospermia (OA) and served as "normal" controls. The remaining biopsies were from men with non-obstructive azoospermia, having hypospermatogenesis of varying etiologies (maturation arrest, Sertoli cell only syndrome, hypospermatogenesis, varicocele). Seventy percent (25/36) of men with non-obstructive azoospermia tested expressed only L-VDCC α1C transcripts containing microdeletions. These findings are summarized in Table 1.

TABLE 1

Extended analysis of L-VDCC mRNA structure in testis biopsies from infertility patients

| I.D. No. | Diagnosis | GAPDH amplicon | L-VDCC amplicon number |
|---|---|---|---|
| 1 | OA | Present | 1,3,5 |
| 2 | OA | Present | 1,3,5 |
| 3 | OA | Present | 1,3,5 |
| 4 | MA | Present | 1 |
| 5 | MA | Present | 5 |
| 6 | MA | Present | 5 |
| 7* | SCO | Present | 4 |
| 8 | SCO | Present | No amplicons detected |
| 9 | SCO | Present | 2 |
| 10 | SCO | Present | 1 |
| 11 | SCO | Present | 3 |
| 12 | SCO | Present | 2 |
| 13 | SCO | Present | 2,3 |
| 14 | HS | Present | 2 |
| 15 | HS | Present | 5 |
| 16 | HS | Present | 2 |
| 17 | HS | Present | 2 |
| 18 | HS | Present | 5 |
| 19 | HS | Present | No amplicons detected |
| 20 | HS | Present | 4 |
| 21 | HS | Present | 1 |
| 22 | HS | Present | 3 |
| 23 | HS | Present | 3 |
| 24 | HS | Present | 4 |
| 25 | VAR/HS | Present | 3 |
| 26 | VAR/HS | Present | 3 |
| 27 | VAR | Present | 4 |
| 28 | VAR/HS | Present | 2 |
| 29 | VAR | Present | 1 |
| 30 | VAR/HS | Present | 2 |
| 31 | VAR/HS | Present | 5 |
| 32 | VAR | Present | 1 |
| 33 | VAR/HS | Present | 4 |
| 34 | VAR/HS | Present | 1 |
| 35 | VAR/HS | Present | 2,3 |
| 36 | VAR | Present | 1,3,5 |
| 37 | VAR/HS | Present | 1,3,5 |
| 38 | VAR | Present | 1,3,5 |
| 39 | VAR/HS | Present | 5 |

OA, obstructive azospermia; MA, maturation arrest; SCO, Sertoli cell only syndrome; HS, hypospermatogenesis; VAR, varicocele OA obstructive azoospennia; MA, maturation arrest; SCO, Sertoli cell only syndrome; HS, hypospermatogenesis; VAR, varicocele Example 4

Then it was analyzed whether the absence of an undeleted LVDCC α1C transcript was predictive of hypospermatogenesis (HS). The results indicated that the absence of an undeleted LVDCC α1C transcript was predictive of HS (Table 2).

TABLE 2

Examination of the relationship between undeleted L-VDCC transcripts and hypospermatogenesis.

| 532 bp | | Hypospermatogenesis | |
|---|---|---|---|
| | | Yes | No |
| L-VDCC amplicon | Yes | 4 | 9 |
| | No | 21 | 1 |

Kappa=−0.544, 95% confidence interval, −0.851 to −0.237, Fisher's exact test, P<0.0001

Example 5

Then it was analyzed whether the absence of an undeleted L-VDCC α1C transcript was predictive of fertilization failure after intracytoplasmic sperm injection (ICSI). The results indicated that the absence of an undeleted LVDCC α1C transcript was not predictive of fertilization failure after ICSI (Table 3).

TABLE 3

Examination of the relationship between L-VDCC microdeletions and fertilization failure after ICSI.

| 532 bp | | Fertilization by ICSI | |
|---|---|---|---|
| | | Yes | No |
| L-VDCC amplicon | Yes | 7 | 1 |
| | No | 8 | 2 |

Kappa=0.069, 95% confidence interval, −0.24 to +0.38, Fisher exact test, P=1.0, N.S.

Example 6

Then it was analyzed whether the absence of an undeleted LVDCC α1C transcript was predictive of pregnancy failure after ICSI. The results indicated that such an absence was predictive of pregnancy failure after ICSI (Table 4).

TABLE 4

Examination of the relationship between L-VDCC microdeletions and pregnancy failure after ICSI.

| 532 bp | | Pregnancy and live birth | |
|---|---|---|---|
| | | Yes | No |
| L-VDCC amplicon | Yes | 5 | 2 |
| | No | 0 | 7 |

Kappa=0.727, 95% confidence interval, 0.39–1.00, Fisher's exact test, P<0.0007

Taken together, the results shown in Examples 3, 4, 5 and 6 indicate that assessment of L-VDCC α1C transcript structure permits identification of hypospermatogenic states as well as identification of patients whose sperm may express defects associated with normal embryo development. Further details about the analyses conducted in these examples may be found in Marmar, J. L., Millan, C., Hurley, I. R., Benoff, S., Detection of microdeletions of the L-type calcium channel within testicular tissue: Should these men have ICSI? In: Robaire, B., Chemes, H., Morales, C. R., eds. Andrology in the $21^{st}$ Century, Proceedings of the VII International Congress on Andrology, Short Communications, Englewood, N.J.: Medimond Publishing Co. Inc. 2001:397–401.

Example 7

It was then examined whether the absence of an undeleted L-VDCC α1C transcript is predictive of the outcome of varicocele repair, meaning will spermatogenic output be increased following surgery? The results indicated that the absence of an undeleted L-VDCC α1C transcript is predictive of the outcome of varicocele repair. The effect of varicocele repair on sperm count was examined in a subset (n=11) of the men examined in Table 1. Those expressing an undeleted LVDCC α1C transcript exhibited a greater than 50% increase in sperm in the ejaculate after varicocele surgery while sperm count was unchanged in those subjects expressing only deleted L-VDCC α1C transcripts (t-test, P<0.02).

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for predicting whether sperm of a patient with hypospermatogenesis associated infertility has defects which are associated with pregnancy failure, said method comprising demonstrating in the patient the presence or absence of an undeleted form of exons 6, 7, 8 or 9 of an L-VDCC α1c transcript, wherein the absence of the undeleted form of the transcript indicates that the sperm of the patient has the defects.

2. The method of claim 1, comprising:

obtaining a suitable tissue sample from the patient;

preparing from the tissue sample a nucleic acid sample; and probing or analyzing the nucleic acid sample for the presence or absence of said undeleted form of said transcript.

3. The method of claim 2, wherein said probing is performed using an oligonucleotide probe having the sequence of SEQ ID NO:7.

4. The method of claim 2, wherein said probing is performed using an oligonucleotide probe having the sequence of SEQ ID NO:8.

5. The method of claim 2, wherein said probing is performed using an oligonucleotide probe having the sequence of SEQ ID NO:9.

6. The method of claim 2, wherein said probing is performed using an oligonucleotide probe having the sequence of SEQ ID NO:10.

7. The method of claim 2, wherein said probing is performed using an oligonucleotide probe having the sequence of SEQ ID NO:11.

8. The method of claim 2, wherein said probing is performed using an oligonucleotide probe having the sequence of SEQ ID NO:12.

9. The method of claim 2, wherein said probing is performed using an oligonucleotide probe having the sequence of SEQ ID NO:13.

10. The method of claim 2, wherein said probing is performed using an oligonucleotide probe having the sequence of SEQ ID NO:14.

11. The method of claim 2, wherein said probing is performed using an oligonucleotide probe having the sequence of SEQ ID NO:15.

12. The method of claim 2, wherein said probing is performed using an oligonucleotide probe having the sequence of SEQ ID NO:16.

13. The method of claim 2, wherein said probing is performed using a temperature that is at or less than 10° C. below the melting temperature of a perfect hybrid formed between a probe and said transcript.

14. The method of claim 2, wherein said probing is performed between 42° C. and 60° C.

15. The method of claim 2, wherein prior to said probing or analysis, said transcript is amplified.

16. The method of claim 15, wherein said transcript is amplified by PCR.

17. The method of claim 16, wherein the PCR amplification is carried out using at least one oligonucleotide primer selected from the group of primers consisting of SEQ ID NO: 1, SEQ ID NO: 2, SEQ ID NO: 3, and SEQ ID NO: 4.

18. The method of claim 16, wherein the PCR amplification is carried out using at least one forward primer and at least one reverse primer.

19. The method of claim 16, wherein the PCR amplification is carried out using SEQ ID NO: 1 and SEQ ID NO: 2.

20. The method of claim 16, wherein the PCR amplification is carried out using SEQ ID NO: 3 and SEQ ID NO: 4.

21. The method of claim 2, wherein the tissue sample is a testis biopsy.

22. The method of claim 21, wherein a testis biopsy is obtained from both testes.

* * * * *